US008232240B2

(12) United States Patent
Cunningham et al.

(10) Patent No.: US 8,232,240 B2
(45) Date of Patent: Jul. 31, 2012

(54) INHIBITORS OF ENVELOPED VIRUS INFECTIVITY

(75) Inventors: James Cunningham, Wellesley, MA (US); Kartik Chandran, Newton, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 136 days.

(21) Appl. No.: 11/884,901

(22) PCT Filed: Feb. 23, 2006

(86) PCT No.: PCT/US2006/006147

§ 371 (c)(1), (2), (4) Date: Aug. 18, 2008

(87) PCT Pub. No.: WO2006/091610

PCT Pub. Date: Aug. 31, 2006

(65) Prior Publication Data

US 2009/0053263 A1 Feb. 26, 2009

Related U.S. Application Data

(60) Provisional application No. 60/655,292, filed on Feb. 23, 2005.

(51) Int. Cl.
*A61K 38/00* (2006.01)
*A61K 39/12* (2006.01)

(52) U.S. Cl. ...................................... 514/1.1; 424/204.1

(58) Field of Classification Search ........................ None
See application file for complete search history.

(56) References Cited

U.S. PATENT DOCUMENTS

| | | | | |
|---|---|---|---|---|
| 6,159,500 | A * | 12/2000 | Demopoulos et al. | 424/456 |
| 6,734,192 | B1 * | 5/2004 | Keller | 514/311 |
| 2003/0166573 | A1 * | 9/2003 | Ohmoto et al. | 514/19 |
| 2003/0224015 | A1 * | 12/2003 | Hart et al. | 424/199.1 |
| 2004/0122058 | A1 * | 6/2004 | Bevec et al. | 514/341 |

FOREIGN PATENT DOCUMENTS

| | | |
|---|---|---|
| WO | WO 91/08769 | 6/1991 |
| WO | WO 92/01451 A1 * | 2/1992 |
| WO | WO 2004/092360 | 10/2004 |
| WO | WO 2005/011649 | 2/2005 |

OTHER PUBLICATIONS

Björck et al., J. Virology, 1990, 64(2):941-943.*
Baize et al., Apoptosis, 2000, 5:5-7.*
Wool-Lewis et al., Journal of Virology, 1998, 72(4):3155-3160.*
Chung et al., Korean Biochem. J., 1986, 19(1):93-98.*
Bogyo et al., Chemistry and Biology, 2000, 7:27-39.*
Chandran, K. et al. 2005, "Endosomal Proteolysis of the Ebola Virus Glycoprotein is Necessary for Infection," Science, 308: 1643-1645.
Collins, A. R. and Grubb A.; 1991, "Inhibitory Effects of Recombinant Human Cystatin C on Human Coronaviruses," Antimicrobial Agents and Chemotherapy, 35:11; 2444-2446.
Database WPI Week 199321, Derwent Publications Ltd. London, GB, AN 1993-172630, (1993).
Fumo G., et al., 2004, "17-Allylamino-17-demothoxygeldanamycin (17-AAG) is effective in down-regulating mutated, constitutvely activated KIT protein in human mast cells," Blood, 103:3; 1078-1084.
Huang, I. et al., 2005, "SARS Coronavirus, but not Human Coronavirus NL63, Utilizes cathepsin L to Infect ACE2-Expressing Cells," Am. Soc. Biochemistry & Molecular Biology, Inc., 16 pages.
Kim, J.C. et al., 1995, "Coronavirus Protein Processing and RNA Synthesis is Inhibited," Virology, 208; 1-8.
Pager C. T and Dutch R. E., "Cathepsin L is Involved in Proteolytic Processing of the Hendra Virus Fusion Protein," J of Virology, 79:20; 12714-12720, (2005).
Simmons G. et al. 2005, "Inhibitors of cathepsin L prevent severe acute respiratory syndrome coronavirus entry," PNAS, 102:33; 11876-11881.
Teng, H. et al., 1999, "Expression of Murine Coronavirus Recombinant Papain-Like Proteinase: Efficient Cleavage is Dependent on the Lengths of both the Substrate and the Proteinase Polypeptides," J. of Virology, 73:4; 2658-2666.
Warfield, K. L. et al., 2006, "Gene-Specific Countermeasures against Ebola Virus Based on Antisense Phosphorodiamidate Morpholino Oligomers," PLoS Pathogens, 2:1; 5-13.
International Search Report, PCT/US2006/006147, Date mailed Mar. 12, 2007.
Kromdijk, W. et al., "Treatment of HIV infection with the CCR5 antagonist maraviroc," Expert Opinion on Pharmacotherapy, 11(7):1215-1223; 2010.
Llibre J. M., "First-line boosted protease inhibitor-based regimens in treatment-naive HIV-1-infected patients—making a good thing better," AIDS Rev. (4):215-22; 2009.
Chandran et al., Endosomal Proteolysis of the Ebola Virus Glycoprotein Is Necessary for Infection; Science 308, 1643-1645 (2005).
Choe et al. Structural interactions between chemokine receptors, gp120 Env and CD4; seminars in Immunology, vol. 10, 249-257 1998.
Haim et al.; Soluble CD4 and CD4-Mimetic Compounds Inhibit HIV-1 Infection by Induction of a Short-Lived Activated State; vol. 5, Issue 4, Jan. 13, 2009.
Harrison, S. Viral membrane fusion; Nature Structural & Molecular Biology; vol. 15 No. 7; 690-698 2008.
Hood et al., Biochemical and Structural Characterization of Cathepsin L-Processed Ebola Virus Glycoprotein: Implications for Viral Entry and Immunogenicity; J of Virology, vol. 84, No. 6; 2972-2982 2010.
Kaletsky et al., Proteolysis of the Ebola Virus Glycoproteins Enhances Virus Binding and Infectivity J of Virology, vol. 81, No. 24 13378-13384 2007.

(Continued)

*Primary Examiner* — Stacy B. Chen
(74) *Attorney, Agent, or Firm* — Wolf, Greenfield & Sacks, P.C.

(57) ABSTRACT

The present invention relates to treatment of infection by enveloped viruses through the use of papain-like cysteine protease inhibitors and kits thereof. Specifically, methods for treatment of filoviruses as well as other enveloped viruses such as Nipah, in particular using cathepsin inhibitors are described.

12 Claims, 15 Drawing Sheets

OTHER PUBLICATIONS

Matsuno et al., Different Potential of C-Type Lectin-Mediated Entry between Marburg Virus Strains; J of Virology, vol. 84, No. 10; 5140-5147 2010.

Qian et al., HIV Entry Inhibitors and Their Potential in HIV Therapy, Medicinal Research Reviews; vol. 29 Issue 2, 369-393 2008.

Sadaghiani et al., Design, Synthesis, and Evaluation of In Vivo Potency and Selectivity of Epoxysuccinyl-Based Inhibitors of Papain-Family Cysteine Proteases; Chemistry & Biology 14, 499-511, 2007.

Schornberg et al., Role of Endosomal Cathepsins in Entry Mediated by the Ebola Virus Glycoprotein J of Virology, vol. 80, No. 8, 4174-4178 2006.

Schornberga et al., $\alpha_5\beta_1$-Integrin controls ebolavirus entry by regulating endosomal cathepsins; PNAS, vol. 106 No. 19, 8003-8008, 2009.

Stoch et al., Effect of the Cathepsin K Inhibitor Odanacatib on Bone Resorption Biomarkers in Healthy Postmenopausal Women: Two Double-Blind, Randomized, Placebo-Controlled Phase I Studies; Clinical pharmacology & Therapeutics; vol. 86 No. 2; 175-182 2009.

Suleiman et al., Vicriviroc in Combination Therapy with an Optimized Regimen for Treatment-Experienced Subjects: 48-Week Results of the VICTOR-E1 Phase 2 Trial; JID 201 590-599 2010.

Tscherne et al., Time-and Temperature-Dependent Activation of Hepatitis C Virus for Low-pH-Triggered Entry J of Virology, vol. 80, No. 4 1734-1741, 2006.

Wensing et al., Fifteen years of HIV Protease Inhibitors: raising the barrier to resistance; Antiviral Research 85 59-74 2010.

Misasi, J. et al., 2012, "Filoviruses Require Endosomal Cysteine Proteases for Entry But Exhibit Distinct Protease Preferences," J. Virol. doi:10.1128/JVL.06346-11.

* cited by examiner

Filovirus Phylogeny

```
                ┌─ Marburg '67
          ┌─98┬─ Marburg '80
     ┌─100┤ 56└─ Marburg '75
     │    └─── Marburg '87
     │
0.1  │                      ┌─ Zaire '76
     │                    ┌─┤┌─ Zaire '96 (Oct.)
     │              ┌─97──┤100─ Zaire '96 (Feb.)
     │              │     │ 64┌─ Zaire '94
     │              │     │   └─ Zaire '95
     └──────100─────┤     └─── Cote d'Ivoire '94
                    │           ┌─ Sudan '76
                    │        ┌100┴─ Sudan '79
                    └──100───┤  69┌─ Reston '92 (Philippines)
                             └100─┤   └─ Reston '92 (Siena)
                                  75┌─ Reston '96
                                   100└─ Reston '89
```

FIGURE 5A
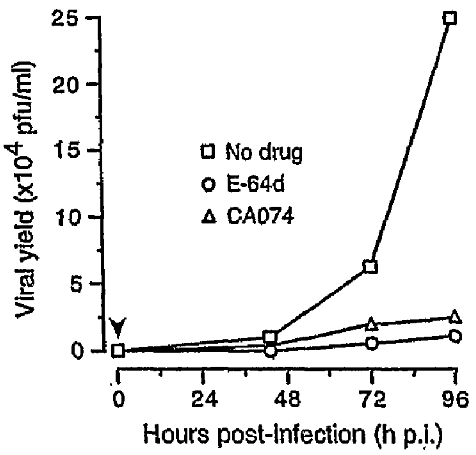
FIGURE 5B
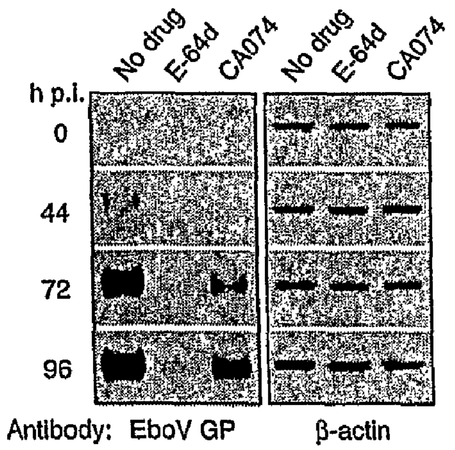
FIGURE 5

| Virus: | | Activity in cells: |
|---|---|---|
| GP1 / 18K | (full bar ~100) | B 100% / L 100% |
| GP1 / 18K | (GP1 short, 18K ~1) | B 10% / L 0% |
| GP1 / 18K | (both ~0.5) | B 10% / L 100% |
| GP1 / 18K | (both ~0.02) | B 0% / L 0% |

Relative Infectivity (% iu/ml)

INHIBITORS OF ENVELOPED VIRUS INFECTIVITY

RELATED APPLICATIONS

This application is a national stage application of PCT/US2006/006147 which claims priority under 35 U.S.C. §119 (e) to U.S. Provisional Application Ser. No. 60/655,292, entitled "INHIBITORS OF ENVELOPED VIRUS INFECTIVITY" filed on Feb. 23, 2005.

FEDERALLY SPONSORED RESEARCH

This invention was made in part with Government support under NIH grant number 5 U54 AI057159. Accordingly, the Government may have certain rights in this invention.

FIELD OF THE INVENTION

The present invention relates to treatment of infection by enveloped viruses through the use of papain-like cysteine protease inhibitors and related compositions and kits thereof.

BACKGROUND OF THE INVENTION

Ebola (EboV) and Marburg viruses are members of the Filoviridae family of enveloped viruses with nonsegmented negative-sense RNA genomes (Geisbert, et al., *Nat. Med.* 10, S110 (2004)). EboV Marburg virus infections are initiated by fusion between viral and host cell membranes, which is mediated by the viral membrane glycoprotein, GP (Wool-Lewis, et al., *J. Virol.* 72, 3155 (1998); and Takada et al., *Proc. Natl. Acad. Sci. USA* 94, 14764 (1997)). Mature GP is a trimer of three disulfide-linked GP1-GP2 heterodimers generated by proteolytic cleavage of the GP0 precursor polypeptide during virus assembly (Volchkov, *Curr. Top. Microbiol. Immunol.* 235, 35 (1999); Sanchez et al., *J. Virol.* 72, 6442 (1998); and Jeffers, et al., *J. Virol.* 76, 12463 (2002)). The membrane-distal subunit, GP1, mediates viral adhesion to host cells and is proposed to regulate the transmembrane subunit GP2, which carries out membrane fusion (Weissenhorn, et al., *Mol. Cell* 2, 605 (1998); Ito, et al., *J. Virol.* 73, 8907 (1999); and Simmons et al., *Virology* 305, 115 (2003)). The processing and function of EboV and Marburg GP are analogous to those of other "type I" envelope glycoproteins, such as human immunodeficiency virus (HIV) Env and influenza virus HA (Volchkov, *Curr. Top. Microbiol. Immunol.* 235, 35 (1999); Weissenhorn, et al., *Mol Cell* 2, 605 (1998); Skehel, et al., *Annu. Rev. Biochem.* 69, 531 (2000); Earp, et al., *Curr. Top. Microbiol. Immunol.* 285, 25 (2005); and Malashkevich et al., *Proc. Natl. Acad. Sci. USA* 96, 2662 (1999)). Based on current models of infection by these viruses (Earp, et al., *Curr. Top. Microbiol. Immunol.* 28525 (2005)), a specific signal within susceptible cells, such as receptor binding or exposure to acidic pH, triggers destabilization of inter-subunit contacts, conformational rearrangement of the transmembrane subunits, and membrane fusion. EboV/Marburg GP1 is believed to function as a clamp that prevents premature deployment of the GP2 membrane fusion machinery and as a sensor for the triggering signal.

The triggering signal for the EboV Marburg GP1-GP2 trimer is unknown. Specifically, an essential EboV receptor analogous to CD4/CCR5 for HIV Env has not been identified (Simmons et al., *J. Virol.* 77, 13433 (2003)). EboVinfection is blocked by inhibitors of endosomal acidification (Wool-Lewis, et al., *J. Virol.* 72, 3155 (1998); and Takada et al., *Proc. Natl. Acad. Sci. USA* 94, 14764 (1997)), indicating that this virus uses an acid-dependent pathway to enter cells. However, acidic pH does not induce GP-dependent cell membrane fusion (Takada et al., *Proc. Natl. Acad. Sci. USA* 94, 14764 (1997)), as might be expected from studies of acidic pH-triggered influenza virus and retroviruses (Boulay, et al., *EMBO J.* 6, 2643 (1987); and Mothes, et al., *Cell* 103, 679 (2000)).

SUMMARY OF THE INVENTION

One aspect of the invention is a method for treating infection by an enveloped virus in a subject, comprising administering to a subject in need thereof a papain-like cysteine protease inhibitor in an effective amount for treating the infection.

In one embodiment of the invention, the papain-like cysteine protease inhibitor is a cathepsin inhibitor, such as a cathepsin-B inhibitor, cathepsin-L inhibitor, cathepsin-S inhibitor, cathepsin-F inhibitor, cathepsin-X inhibitor, cathepsin-K inhibitor, cathepsin-V inhibitor, cathepsin-W inhibitor, cathepsin-C inhibitor, cathepsin-O inhibitor, and/or cathepsin-H inhibitor. In another embodiment of the invention, the papain-like cysteine protease inhibitor is one or more of epoxysuccinyl peptide derivatives [E-64, E-64a, E-64b, E-64c, E-64d, CA-074, CA-074 Me, CA-030, CA-028, etc.], peptidyl aldehyde derivatives [leupeptin, antipain, chymostatin, Ac-LVK-CHO, Z-Phe-Tyr-CHO, Z-Phe-Tyr(OtBu)-COCHO.H2O, 1-Naphthalenesulfonyl-Ile-Trp-CHO, Z-Phe-Leu-COCHO.H2O, etc.], peptidyl semicarbazone derivatives, peptidyl methylketone derivatives, peptidyl trifluoromethylketone derivatives [Biotin-Phe-Ala-fluoromethyl ketone, Z-Leu-Leu-Leu-fluoromethyl ketone minimum, Z-Phe-Phe-fluoromethyl ketone, N-Methoxysuccinyl-Phe-HOMO-Phe-fluoromethyl ketone, Z-Leu-Leu-Tyr-fluoromethyl ketone, Leupeptin trifluoroacetate, ketone, etc.], peptidyl halomethylketone derivatives [TLCK, etc.], bis(acylamino)ketone [1,3-Bis(CBZ-Leu-NH)-2-propanone, etc.], peptidyl diazomethanes [Z-Phe-Ala-CHN2, Z-Phe-Thr(OBzl)-CHN2, Z-Phe-Tyr (O-t-But)-CHN2, Z-Leu-Leu-Tyr-CHN2, etc.], peptidyl acyloxymethyl ketones, peptidyl methylsulfonium salts, peptidyl vinyl sulfones [LHVS, etc.], peptidyl nitriles, disulfides[5,5'-dithiobis[2-nitrobenzoic acid], cysteamines, 2,2'-dipyridyl disulfide, etc.], non-covalent inhibitors [N-(4-Biphenylacetyl)-S-methylcysteine-(D)-Arg-Phe-b-phenethylamide, etc.], thiol alkylating agents [maleimides, etc,], azapeptides, azobenzenes, O-acylhydroxamates [Z-Phe-Gly-NHO-Bz, Z-FG-NHO-BzOME etc.], lysosomotropic agents [chloroquine, ammonium chloride, etc.], or inhibitors based on Cystatins [Cystatins A, B, C, stefins, kininogens, Procathepsin B Fragment 26-50, Procathepsin B Fragment 36-50, etc.].

In one embodiment of the invention, the subject has or is at risk of infection by a single-stranded enveloped RNA virus. In another embodiment of the invention, the subject has or is at risk of infection by a Type I enveloped virus. In yet another embodiment, the Type I enveloped virus is a filovirus. In still another embodiment, the filovirus is an Ebola virus or a Marburg virus. In yet another embodiment, the Type I enveloped virus is a orthomyxovirus. In still another embodiment, the Type I enveloped virus is a paramyxovirus. In still another embodiment, the Type I enveloped virus is an arenavirus.

In another embodiment of the invention, the subject has or is at risk of infection by a virus such as but not limited to flavivirus such as hepatitis-C virus, bunyavirus, poxvirus, herpesvirus, hepadnavirus, rhabdovirus, bornavirus, arterivirus or togavirus.

In one embodiment of the invention, the papain-like cysteine protease inhibitor is administered orally. In another embodiment of the invention, the papain-like cysteine protease inhibitor is administered intravenously. In yet another embodiment, multiple doses of the papain-like cysteine protease inhibitor are administered. In still another embodiment, the papain-like cysteine protease inhibitor is administered every 12 hours. In still another embodiment, the papain-like cysteine protease inhibitor is administered in combination with another protease inhibitor. In another embodiment of the invention, the papain-like cysteine protease inhibitor is administered in combination with an anti-viral agent. In another embodiment, the papain-like cysteine protease inhibitor is administered in combination with an anti-viral vaccine.

In one embodiment of the invention, the subject is a human. In another embodiment, the subject is a non-human animal.

Another aspect of the invention is a kit comprising a container housing a papain-like cysteine protease inhibitor and instructions for administering the papain-like cysteine protease inhibitor to a subject having or at risk of having infection by an enveloped virus. In one embodiment, the papain-like cysteine protease inhibitor is a cathepsin inhibitor. In another embodiment, the papain-like cysteine protease inhibitor is a cathepsin inhibitor, such as a cathepsin-B inhibitor, cathepsin-L inhibitor, cathepsin-S inhibitor, cathepsin-F inhibitor, cathepsin-X inhibitor, cathepsin-K inhibitor, cathepsin-V inhibitor, cathepsin-W inhibitor, cathepsin-C inhibitor, cathepsin-O inhibitor, and/or cathepsin-H inhibitor. In another embodiment of the invention, the papain-like cysteine protease inhibitor is one or more of epoxysuccinyl peptide derivatives [E-64, E-64a, E-64b, E-64c, E-64d, CA-074, CA-074 Me, CA-030, CA-028, etc.], peptidyl aldehyde derivatives [leupeptin, antipain, chymostatin, Ac-LVK-CHO, Z-Phe-Tyr-CHO, Z-Phe-Tyr(OtBu)-COCHO.H2O, 1-Naphthalenesulfonyl-Ile-Trp-CHO, Z-Phe-Leu-COCHO.H2O, etc.], peptidyl semicarbazone derivatives, peptidyl methylketone derivatives, peptidyl trifluoromethylketone derivatives [Biotin-Phe-Ala-fluoromethyl ketone, Z-Leu-Leu-Leu-fluoromethyl ketone minimum, Z-Phe-Phe-fluoromethyl ketone, N-Methoxysuccinyl-Phe-HOMO-Phe-fluoromethyl ketone, Z-Leu-Leu-Tyr-fluoromethyl ketone, Leupeptin trifluoroacetate, ketone, etc.], peptidyl halomethylketone derivatives [TLCK, etc.], bis(acylamino)ketone [1,3-Bis(CBZ-Leu-NH)-2-propanone, etc.], peptidyl diazomethanes [Z-Phe-Ala-CHN2, Z-Phe-Thr(OBzl)-CHN2, Z-Phe-Tyr (O-t-But)-CHN2, Z-Leu-Leu-Tyr-CHN2, etc.], peptidyl acyloxymethyl ketones, peptidyl methylsulfonium salts, peptidyl vinyl sulfones [LHVS, etc.], peptidyl nitriles, disulfides[5,5'-dithiobis [2-nitrobenzoic acid], cysteamines, 2,2'-dipyridyl disulfide, etc.], non-covalent inhibitors [N-(4-Biphenylacetyl)-S-methylcysteine-(D)-Arg-Phe-b-phenethylamide, etc.], thiol alkylating agents [maleimides, etc,], azapeptides, azobenzenes, O-acylhydroxamates [Z-Phe-Gly-NHO-Bz, Z-FG-NHO-BzOME etc.], lysosomotropic agents [chloroquine, ammonium chloride, etc.]. Inhibitors based on Cystatins [Cystatins A, B, C, stefins, kininogens, Procathepsin B Fragment 26-50, Procathepsin B Fragment 36-50 etc.], or in another embodiment of the invention, the instructions specify that the papain-like cysteine protease inhibitor is administered to a subject having or at risk of having an infection with a Type I enveloped virus.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF DRAWINGS

This application includes examples which refer to figures or other drawings. It is to be understood that the referenced figures are illustrative only and are not essential to the enablement of the claimed invention.

FIG. 2B (bottom panel) is a graph showing CatB and Cathepsin L (CatL) enzymatic activities in CA074-treated cells.

FIGS. 4A and B are images of immunoblots of SDS-PAGE protein gels showing that purified CatB (FIG. 4A) and CatL (FIG. 4B) cleave EboV Zaire GPΔM to an ~18K polypeptide ($GP1_{18K}$). Virus was incubated with enzyme for 1 h at pH 5.5 and 37° C. Untreated virus containing GP1Zaire ΔM (open arrowhead) and CatL-treated virus containing $GP1_{18K}$ (18K) (filled arrowhead) were used in panels C-D. The x-axes are concentration of inhibitor in μg/ml, and the y-axes are relative molecular weight of GP1 and cleavage products. FIG. 4C is a graph showing that virus containing $GP1_{18K}$ is highly infectious and fully dependent upon cellular CatB activity. Vero cells were left untreated (filled bars) or pretreated with E-64d (300 μM) (open bars) to inactivate CatB. Approximate CatB activity (B %) in these cells is indicated above the bars. The y-axis is relative infectivity in % iu/ml. FIG. 4D is a graph showing that virus containing $GP1_{18K}$ dramatically bypasses a block to GP1ΔM cleavage within cells. Cells were treated with inhibitors to obtain the approximate levels of cellular CatB (B %) and CatL (L %) activity shown. Open bars, 300 μM E-64d. Filled black bars, 10 μM FYdmk. Filled grey bars, 40 μM CA074. Striped bars, 1 μM FYdmk. Cells were then infected with virus containing GP1ΔM only, $GP1_{18K}$ only, or increasing amounts of $GP1_{18K}$ (wedge). The y-axis is relative infectivity in % iu/ml. FIG. 4E is an image of a protein gel showing that purified CatB efficiently cleaves $GP1_{18K}$. Virus was incubated with the indicated enzymes for 1 h at pH 5.5 and 37° C. CatB, 40 μg/ml. CatL, 20 μg/ml. CatB and CatL together (CatB+CatL). CatL followed by CatB (CatL→CatB) (30 min each). The x-axis is relative molecular weight. FIG. 4F is a graph showing that cleavage of $GP1_{18K}$ by CatB inactivates virus. The y-axis is relative infectivities of viruses from panel E in % iu/ml. Error bars, s.d. (n=3).

FIG. 5 provides two graphs showing that endosomal cysteine protease inhibitors diminish EboV-Zaire multiplication. FIG. 5A is a graph showing yields of infectious EboV-Zaire released from Vero cells treated with 300 μM E-64d (to inactivate papain like cysteine proteases), or 80 μM CA074 (to selectively inactivate CatB) for 4 h. Growth medium containing inhibitors was removed from cells at the indicated time (arrowhead) and replaced with fresh medium lacking inhibitors. pfu/ml, plaque-forming units per ml. The y-axis is EboV Zaire yield in ×104 pfu/ml, and the x-axis is hours post-infection (h p.i.). (FIG. 5B is an image of an immunoblot of an SDS-PAGE of virus and cell proteins showing GP expression in EboV Zaire-infected cells from panel A. β-actin was used as a loading control.

DETAILED DESCRIPTION

Figure 1:
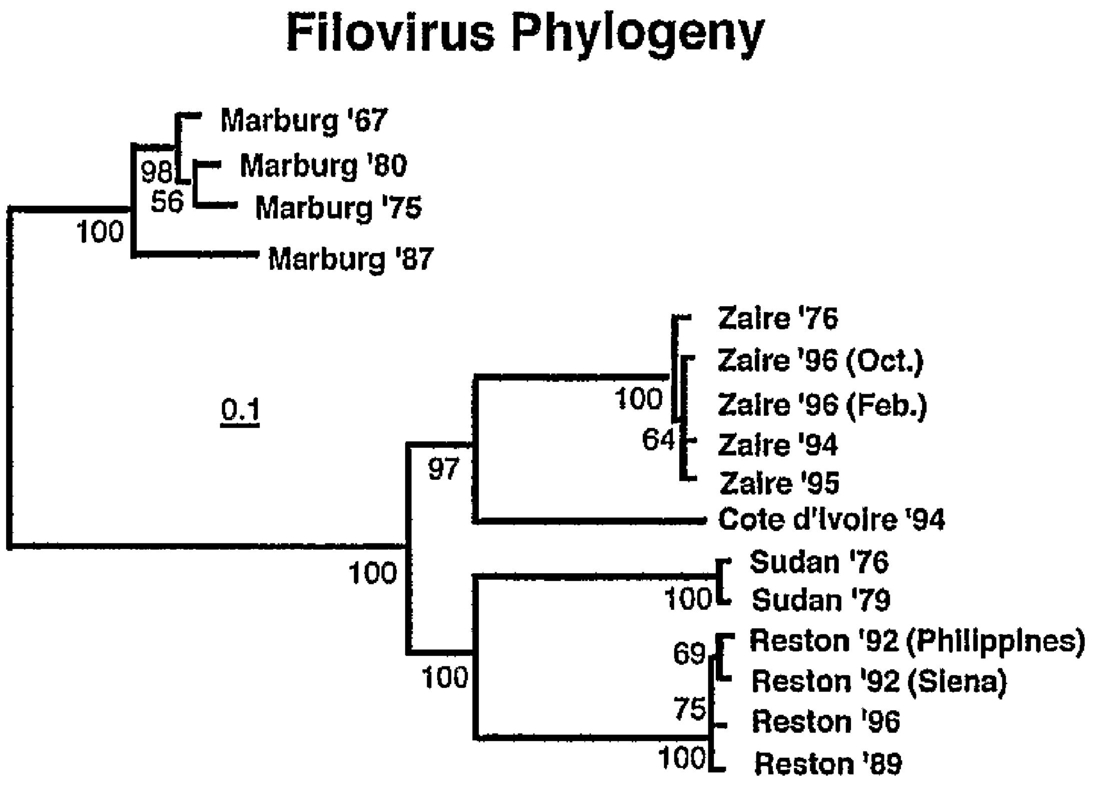
FIG. 1 is a schematic diagram of the filovirus phylogeny, illustrating relative identities amongst closely related filovirus species and their strains. [new]

The invention relates in some aspects to methods of treating viral infection. Papain-like cathepsin inhibitors are useful for treating infection by enveloped viruses.

As shown in the examples below, a new mechanism for activating the enveloped virus fusion machinery has been discovered. The data demonstrate that papain like cysteine proteases are involved in and are important components of the viral entry process. Inhibition of these proteases is sufficient to inhibit enveloped viral entry into a host cell. Thus, the invention relates to the use of cellular protease inhibitors for treating viral infection. The examples focus on a simple model in which cleavage of Ebola virus glycoprotein I (GP1) by cellular cathepsin B (CatB) and cathepsin L (CatL) is demonstrated to be involved in the viral entry process. Previously signals involved in these processes in other enveloped viruses have been shown to be due to binding of viruses to a specific receptor and/or exposure of viruses to acidic pH. The discoveries of the invention suggest that cysteine proteases provide an additional important mechanism by which enveloped viruses, such as Ebola, infect host cells.

In particular, the examples demonstrate that cathepsins such as CatB are sufficient for triggering of enveloped viral membrane fusion within the acidic endosomal milieu of target cells. These findings demonstrated that the endosomal cysteine protease CatB is an essential host factor for Ebola Zaire or Cote d'Ivoire viral infection and either CatB or CatL is essential for infection by Ebola Sudan, Reston or Marburg virus.

Although applicant is not bound by a mechanism, it is believed that the inhibitors of the invention are useful for treating enveloped viral infection by interfering with the critical role by cathepsins of proteolysis of the GP1 glycoprotein subunit to trigger membrane fusion and cell entry. The specific data presented herein suggest that GP1 proteolysis is a multistep process. The initial step in this process is proposed to be cleavage of GP1 by a cathepsin such as (CatB and/or CatL) to remove C-terminal sequences and generate an N terminal $GP1_{18K}$-like species (i.e. see FIGS. 6-7). The C-terminal region of GP1 contains highly variable and heavily glycosylated sequences (Jeffers, et al., *J. Virol.* 76, 12463 (2002)) that promote viral adhesion (Simmons et al., *Virology* 305, 115 (2003)) and may shield viral particles from immune recognition and/or stabilize the prefusion conformation of GP (Chandran, et al., Unpublished observations; and Wahl-Jensen et al., *J. Virol.* 79, 2413 (2005)), but may have to be removed to render GP competent to be triggered by CatB and/or CatL.

Several viruses produce a syndrome referred to as hemorrhagic fever following infection of humans. Although the viruses are not structurally similar, they produce this syndrome in humans, which is characterized by an exaggerated immune response. Often the viruses which produce this type of systemic inflammatory response resulting in hemorrhagic fever have transferred from a different species to humans. Examples of viruses that fall into this category include Ebola, Marburg, Nipah, Hendra, avian-derived influenza. The methods of the invention are particularly useful for treating viruses which cause hemorrhagic fever or similar types of systemic inflammatory responses.

Figure 13:
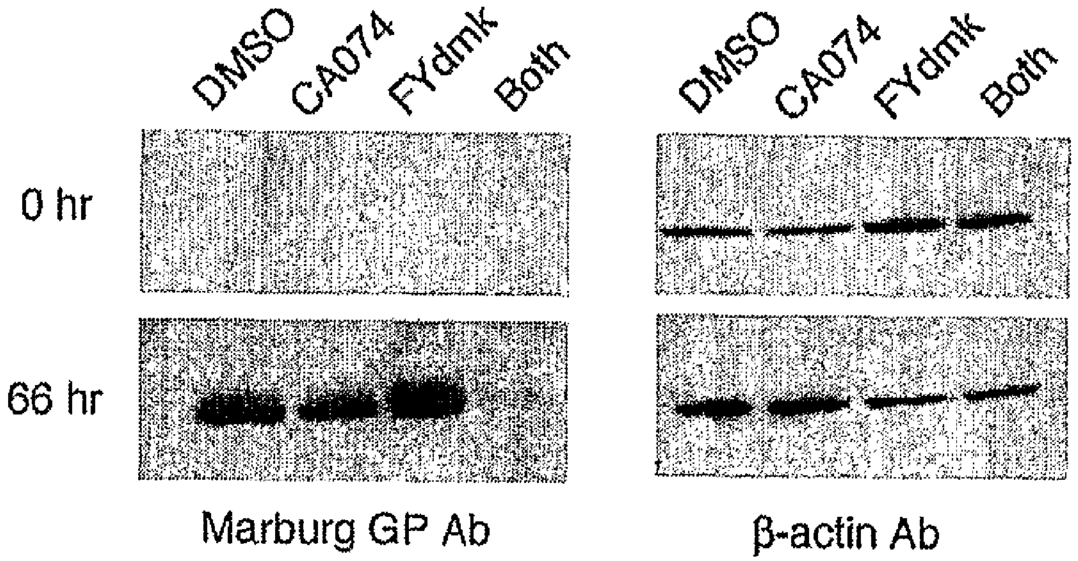
FIG. 13 is a set of immunoblots of Vero cells treated with DMSO or inhibitors that are probed with an antibody against Marburg glycoprotein (left panel) or with an antibody against ββ-actin (to control for cell viability/recovery, right panel). The effects of the CatB inhibitor CA074 (80 μM) and the CatL inhibitor FYdmk(1 μM) in combination, but not each alone to inhibit growth of Marburg virus on Vero cells is demonstrated.

To date, no successful antiviral therapies for Ebola virus (EboV) infection have been identified. To test if papain-like cysteine proteases are potential anti-EboV targets, the effects of cysteine protease inhibitor E-64d and selective CatB inhibitor CA074 on growth of infectious EboV-Zaire were measured. This data is described in detail in the Examples but a brief summary is provided herein. Vero cells were pretreated with these inhibitors and exposed to virus for 1 h. Inhibitor and unbound virus were then removed and viral growth was monitored. The yields of infectious EboV progeny (FIG. 5A) and expression of cell-associated GP1 (FIG. 5B) were markedly reduced in inhibitor-treated cells (FIGS. 5A and 5B) (growth yields were reduced by greater than 90% after 96 h). Thus, EboV multiplication in Vero cells is exquisitely sensitive to inhibitors of papain-like cysteine proteases. This finding was supported by the observation that CatL and CatB inhibitors inhibited growth of Marburg virus (FIG. 13).

The methods of the invention are useful for treating a subject in need thereof. A subject in need thereof is a subject having or at risk of having an enveloped virus infection. In its broadest sense, the terms "treatment" or "to treat" refer to both therapeutic and prophylactic treatments. If the subject in need of treatment is experiencing a condition (i.e., has or is having a particular condition), then "treating the condition" refers to ameliorating, reducing or eliminating one or more symptoms arising from the condition. If the subject in need of treatment is one who is at risk of having a condition, then treating the subject refers to reducing the risk of the subject having the condition or, in other words, decreasing the likelihood that the subject will develop an infectious disease to the virus, as well as to a treatment after the subject has been infected in order to fight the infectious disease, e.g., reduce or eliminate it altogether or prevent it from becoming worse.

Thus the invention encompasses the use of the inhibitors described herein alone or in combination with other therapeutics for the treatment of a subject having or at risk of having a viral infection. A "subject having an enveloped viral infection" is a subject that has had contact with a virus. Thus the virus has invaded the body of the subject. The word "invade" as used herein refers to contact by the virus with an external surface of the subject, e.g., skin or mucosal membranes and/or refers to the penetration of the external surface of the subject by the virus. A subject at risk of having an enveloped virus infection is one that has been exposed to or may become exposed to an enveloped virus or a geographical area in which an enveloped viral infection has been reported. Further risks include close contact with a human or non-human primate or their tissues infected with the virus. Such persons include laboratory or quarantine facility workers who handle non-human primates that have been associated with the disease. In addition, hospital staff and family members who care for patients with the disease are at risk if they do not use proper barrier nursing techniques.

As used herein, a subject includes humans and non-human animals such as non-human primates, dogs, cats, sheep, goats, cows, pigs, horses and rodents.

The invention provides methods and compositions to treat conditions which would benefit from, and which thus can be treated by, an inhibition of papain-like cysteine proteases, such as infection by enveloped viruses.

The inhibitors described herein are isolated molecules. An isolated molecule is a molecule that is substantially pure and is free of other substances with which it is ordinarily found in nature or in vivo systems to an extent practical and appropriate for its intended use. In particular, the molecular species are sufficiently pure and are sufficiently free from other biological constituents of host cells so as to be useful in, for example, producing pharmaceutical preparations or sequencing if the molecular species is a nucleic acid, peptide, or polysaccharide. Because an isolated molecular species of the invention may be admixed with a pharmaceutically-acceptable carrier in a pharmaceutical preparation or be mixed with some of the components with which it is associated in nature, the molecular species may comprise only a small percentage by weight of the preparation. The molecular species is nonetheless substantially pure in that it has been substantially separated from the substances with which it may be associated in living systems.

As used herein, a "papain-like cysteine protease inhibitor" is an agent whose main pharmacological effect is to inhibit the activity of the class of endosomal peptidases that require acidic pH for enzyme activity. Examples of human papain-like cysteine proteases include but are not limited to cathepsin B, cathepsin L, cathepsin S, cathepsin-F, cathepsin-X, cathepsin K, cathepsin V, cathepsin W, cathepsin C, cathepsin O, and cathepsin H. Cathepsin inhibitors useful in non-human animals are often categorized differently but are known to those of skill in the art. Thus, the inhibitors include cathepsin inhibitors which are known to correspond with human cathepsin inhibitors. Inhibitors of these cathepsins, and in some embodiments in particular, cathepsin B, are useful according to methods of the invention. Many cathepsin inhibitors have been described in the literature and are well known and are commercially available.

Examples of papain-like cysteine protease inhibitors include but are not limited to the group consisting of epoxysuccinyl peptide derivatives [E-64, E-64a, E-64b, E-64c, E-64d, CA-074, CA-074 Me, CA-030, CA-028, etc.], peptidyl aldehyde derivatives [leupeptin, antipain, chymostatin, Ac-LVK-CHO, Z-Phe-Tyr-CHO, Z-Phe-Tyr(OtBu)-COCHO.H2O, 1-Naphthalenesulfonyl-Ile-Trp-CHO, Z-Phe-Leu-COCHO.H2O, etc.], peptidyl semicarbazone derivatives, peptidyl methylketone derivatives, peptidyl trifluoromethylketone derivatives [Biotin-Phe-Ala-fluoromethyl ketone, Z-Leu-Leu-Leu-fluoromethyl ketone minimum, Z-Phe-Phe-fluoromethyl ketone, N-Methoxysuccinyl-Phe-HOMO-Phe-fluoromethyl ketone, Z-Leu-Leu-Tyr-fluoromethyl ketone, Leupeptin trifluoroacetate, ketone, etc.], peptidyl halomethylketone derivatives [TLCK, etc.], bis(acylamino)ketone [1,3-Bis(CBZ-Leu-NH)-2-propanone, etc.], peptidyl diazomethanes [Z-Phe-Ala-CHN2, Z-Phe-Thr (OBzl)-CHN2, Z-Phe-Tyr (O-t-But)-CHN2, Z-Leu-Leu-Tyr-CHN2, etc.], peptidyl acyloxymethyl ketones, peptidyl methylsulfonium salts, peptidyl vinyl sulfones [LHVS, etc.], peptidyl nitriles, disulfides[5,5'-dithiobis[2-nitrobenzoic acid], cysteamines, 2,2'-dipyridyl disulfide, etc.], non-covalent inhibitors [N-(4-Biphenylacetyl)-S-methylcysteine-(D)-Arg-Phe-b-phenethylamide, etc.], thiol alkylating agents [maleimides, etc,], azapeptides, azobenzenes, O-acylhydroxamates [Z-Phe-Gly-NHO-Bz, Z-FG-NHO-BzOME etc.], lysosomotropic agents [chloroquine, ammonium chloride, etc.], and inhibitors based on Cystatins [Cystatins A, B, C, stefins, kininogens, Procathepsin B Fragment 26-50, Procathepsin B Fragment 36-50 etc.]. In one embodiment CA-074 is preferred.

The compositions are delivered in effective amounts. The term effective amount refers to the amount necessary or sufficient to realize a desired biologic effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is effective to treat the particular subject. Animals that have been produced to lack cathepsins are not associated with many physiological defects. Thus, toxicity of the inhibitor is expected to be low. The effective amount for any particular application can vary depending on such factors as the disease or condition being treated, the particular inhibitor being administered, the size of the subject, or the severity of the disease or condition. One of ordinary skill in the art can empirically determine the effective amount of a particular inhibitor and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

For any compound described herein the therapeutically effective amount can be initially determined from preliminary in vitro studies and/or animal models. A therapeutically effective dose can also be determined from human data for inhibitors which have been tested in humans and for compounds which are known to exhibit similar pharmacological activities, such as other related active agents. For instance, many cathepsin inhibitors have been extensively studied. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

Thus, the methods of the invention are useful for treating infection with enveloped viruses. Viruses are small infectious agents which contain a nucleic acid core and a protein coat, but are not independently living organisms. A virus cannot multiply in the absence of a living cell within which it can replicate. Viruses enter specific living cells either by transfer across a membrane or direct injection and multiply, causing disease. The multiplied virus can then be released and infect additional cells. Some viruses are DNA-containing viruses and others are RNA-containing viruses. The genomic size, composition and organization of viruses shows tremendous diversity.

As used herein, an "enveloped" virus is an animal virus which possesses a membrane or 'envelope', which is a lipid bilayer containing viral proteins. The envelope proteins of a virus play a pivotal role in its lifecycle. They participate in the assembly of the infectious particle and also play a crucial role in virus entry by binding to a receptor present on the host cell and inducing fusion between the viral envelope and a membrane of the host cell. Enveloped viruses can be either spherical or filamentous (rod-shaped) and include but are not limited to filoviruses, such as Ebola virus or Marburg virus, Arboroviruses such as Togaviruses, flaviviruses (such as hepatitis-C virus), bunyaviruses, and Arenaviruses, Orthomyxoviridae, Paramyxoviridae, poxvirus, herpesvirus, hepadnavirus, Rhabdovirus, Bornavirus, and Arterivirus.

In some embodiments, the invention provides for methods of treating infection by a type I enveloped virus of the family Filoviridae, a family of viruses with a single-stranded, unsegmented (−) sense RNA genome. Filoviruses can cause severe hemorrhagic fever in humans and non-human primates. So far, only two genuses of this virus family have been identified: Marburg and Ebola. Four species of Ebola virus have been identified: Cote d'Ivoire (CI), Sudan (S), Zaire (Z), and Reston (R). The Reston subtype is the only known filovirus that is not known to cause fatal disease in humans; however, it can be fatal in monkeys.

Infection by Ebola virus leads to Ebola Hemorrhagic Fever (EHF), the clinical manifestations of which are severe. The incubation period varies between four and sixteen days. The initial symptoms are generally a severe frontal and temporal headache, generalized aches and pains, malaise, and by the second day the victim will often have a fever. Later symptoms include watery diarrhea, abdominal pain, nausea, vomiting, a dry sore throat, and anorexia. By day seven of the symptoms, the patient will often have a maculopapular (small slightly raised spots) rash. At the same time the person may develop thrombocytopenia and hemorrhagic manifestations, particularly in the gastrointestinal tract, and the lungs, but it can occur from any orifice, mucous membrane or skin site. Ebola causes lesions in almost every organ, although the liver and spleen are the most noticeably affected. Both are darkened and enlarged with signs of necrosis. The cause of death (>75% in most outbreaks) is normally shock, associated with fluid and blood loss into the tissues. The hemorrhagic and connective tissue complications of the disease are not well understood, but may be related to onset of disseminated intravascular coagulation.

As used herein, the term "Marburg virus" refers to the filovirus that causes Marburg hemorrhagic fever. Marburg hemorrhagic fever is a rare, severe type of hemorrhagic fever which affects both humans and non-human primates. The case-fatality rate for Marburg hemorrhagic fever is 70% in recent Angola outbreak. After an incubation period of 5-10 days, the onset of the disease is sudden and is marked by fever, chills, headache, and myalgia. Around the fifth day after the onset of symptoms, a maculopapular rash, most prominent on the trunk (chest, back, stomach), may occur. Nausea, vomiting, chest pain, a sore throat, abdominal pain, and diarrhea then may appear. Symptoms become increasingly severe and may include jaundice, inflammation of the pancreas, severe weight loss, delirium, shock, liver failure, massive hemorrhaging, and multi-organ dysfunction.

The family Orthomyxoviridae includes, without limitation, influenza A virus, influenza B virus, influenza C virus, Thogotovirus, Dhori virus, and infectious salmon anemia virus.

Influenza type A viruses are divided into subtypes based on two proteins on the surface of the virus. These proteins are called hemagglutinin (HA) and neuraminidase (NA). There are 15 different HA subtypes and 9 different NA subtypes. Subtypes of influenza A virus are named according to their HA and NA surface proteins, and many different combinations of HA and NA proteins are possible. For example, an "H7N2 virus" designates an influenza A subtype that has an HA 7 protein and an NA 2 protein. Similarly an "H5N1" virus has an HA 5 protein and an NA 1 protein. Only some influenza A subtypes (i.e., H1N1, H2N2, and H3N2) are currently in general circulation among people. Other subtypes such as H5 N1 are found most commonly in other animal species and in a small number of humans, where it is highly pathogenic. For example, H7N7 and H3N8 viruses cause illness in horses. Humans can be infected with influenza types A, B, and C. However, the only subtypes of influenza A virus that normally infect people are influenza A subtypes H1N1, H2N2, and H3N2 and recently, H5N1.

The family Paramyxoviridae includes, without limitation, human parainfluenza virus, human respiratory syncytial virus (RSV), Sendai virus, Newcastle disease virus, mumps virus, rubeola (measles) virus, Hendra virus, Nipah virus, avian pneumovirus, and canine distemper virus. The family Filoviridae includes, without limitation, Marburg virus and Ebola virus. The family Rhabdoviridae includes, without limitation, rabies virus, vesicular stomatitis virus (VSV), Mokola virus, Duvenhage virus, European bat virus, salmon infectious hematopoietic necrosis virus, viral hemorrhagic septicaemia virus, spring viremia of carp virus, and snakehead rhabdovirus. The family Bornaviridae includes, without limitation, Borna disease virus. The family Bunyaviridae includes, without limitation, Bunyamwera virus, Hantaan virus, Crimean Congo virus, California encephalitis virus, Rift Valley fever virus, and sandfly fever virus. The family Arenaviridae includes, without limitation, Old World Arenaviruses, such as Lassa virus (Lassa fever), Ippy virus, Lymphocytic choriomeningitis virus (LCMV), Mobala virus, and Mopeia virus and New World Arenaviruses, such as Junin virus (Argentine hemorrhagic fever), Sabia (Brazilian hemorrhagic fever), Amapari virus, Flexal virus, Guanarito virus (Venezuela hemorrhagic fever), Machupo virus (Bolivian hemorrhagic fever), Latino virus, Boliveros virus, Parana virus, Pichinde virus, Pirital virus, Tacaribe virus, Tamiami virus, and Whitewater Arroyo virus. The Arenaviridae associated with specific diseases include Lymphocytic choriomeningitis virus (meningitis), Lassa virus (hemorrhagic fever), Junin Virus (Argentine hemorrhagic fever), Machupo Virus (Bolivian hemorrhagic fever), Sabia virus (Brazilian hemorrhagic fever), and Guanarito (Venezuelan Hemorrhagic fever).

The arboviruses are a large group (more than 400) of enveloped RNA viruses that are transmitted primarily (but not exclusively) by arthropod vectors (mosquitoes, sand-flies, fleas, ticks, lice, etc). More recently, the designated Arborviruses have been split into four virus families, including the togaviruses, flaviviruses, arenaviruses and bunyaviruses.

As used herein, the term "togavirus" refers to members of the family Togaviridae, which includes the genuses Alphavirus (e.g. Venezuela equine encephalitis virus, Sindbis virus, which causes a self-limiting febrile viral disease characterized by sudden onset of fever, rash, arthralgia or arthritis, lassitude, headache and myalgia) and Rubivirus (e.g. Rubella virus, which causes Rubella in vertebrates).

Rubella virus infections in adults are frequently sub-clinical. A characteristic pink, continuous maculopapular rash appears in 95% of adolescent patients 14-25 days after infection, and the patient is infectious for most of this time. After early viremia, rubella virus multiplies in many organs, particularly lymph nodes (lymphadenopathy), including the placenta, but symptoms in adults are rare. In children Rubella virus causes a mild febrile illness. The virus crosses placenta and multiplies in the fetus. Up to 85% of infants infected in the first trimester of pregnancy get congenital rubella syndrome (CRS), characterized by low birth weight, deafness, CNS involvement, and possibly abortion, with symptoms worse the earlier in pregnancy they occur.

Flaviviridae is a member of the family of (+)-sense RNA enveloped viruses. Flaviviridae includes flavivirus, Pestivirus, and Hepacivirus. Flavivirus genus including yellow fever virus, dengue fever virus, and Japanese encaphilitis (JE) virus. The Pestivirus genus includes the three serotypes of bovine viral diarrhea, but no known human pathogens. Genus *Hepacivirus* consists of hepatitis C virus and hepatitis C-like viruses.

A yellow fever virus infection is characterized by an incubation period of 3 to 6 days, during which 5% to 50% of infected people develop disease. Yellow fever begins with a nonspecific 1- to 3-day febrile illness, followed by a brief remission, and then by a life-threatening toxic syndrome accompanied by epistaxis, other hemorrhagic phenomena, jaundice, and disseminated intravascular coagulation. Mortality rates for yellow fever are approximately 20%.

There are four serotypes of dengue fever virus, all transmitted by mosquitos. Dengue fever virus infection may be asymptomatic or may result in dengue fever. This is generally a self-limiting febrile illness which occurs after a 4-8 day incubation period. It has symptoms such as fever, aches and arthralgia (pain in the joints) which can progress to arthritis (inflammation of the joints), myositis (inflammation of muscle tissue) and a discrete macular or maculopapular rash. In this situation clinical differentiation from other viral illnesses may not be possible, recovery is rapid, and need for supportive treatment is minimal. Dengue haemorrhagic fever (DHF) is a potentially deadly complication. Dengue hemorrhagic fever commences with high fever and many of the symptoms of dengue fever, but with extreme lethargy and drowsiness. The patient has increased vascular permeability and abnormal homeostasis that can lead to hypovolemia and hypotension, and in severe cases, result in hypovolemic shock often complicated by severe internal bleeding.

The Japanese encephalitis antigenic complex includes Alfuy, Japanese encephalitis, Kokobera, Koutango, Kunjin, Murray Valley encephalitis, St. Louis encephalitis, Stratford, Usutu, and West Nile viruses. These viruses are transmissible by mosquitoes and many of them can cause febrile, sometimes fatal, illnesses in humans. West Nile virus is the most widespread of the flaviviruses, with geographic distribution including Africa and Eurasia. West Nile virus RNA has been detected in overwintering mosquitoes in New York City & the geographic range of the virus is increasing in the USA.

The genus Pestivirus has been divided into bovine viral diarrhea virus (BVDV), classical swine fever virus (CSFV), and border disease virus (BDV). Infection with BVDV results in a variety of diseases ranging from subclinical to highly fatal. Many BVDV viruses cause only clinically mild disease in nonpregnant adult cattle. Prenatal infection can cause congenital malformations and/or fetal death.

The Hepacivirus genus includes the hepatitis C virus (HCV). The majority of cases of HCV infection give rise to an acute illness, where up to 85% of infections may develop into chronic hepatitis. Almost all patients develop a vigorous antibody and cell-mediated immune response which fails to clear the infection but may contribute towards liver damage.

Arenaviridae is a member of the family of (−) sense RNA viruses. As used herein, the term "Arenavirus" refers to members of the genus Arenavirius, a family of viruses whose members are generally associated with rodent-transmitted disease in humans, including Lymphocytic choriomeningitis virus (LCMV), Lassa virus, Junin virus, which causes Argentine hemorrhagic fever, Machupo virus, which causes Bolivian hemorrhagic fever, Guanarito virus, which causes Venezuelan hemorrhagic fever, and Sabia, which causes Brazilian hemorrhagic fever. LCMV causes which causes lymphocytic choriomeningitis, a mild disease that is occasionally severe with hemorrhaging. Infection by LCMV is rare in humans. Lassa virus causes Lassa fever in humans. Signs and symptoms of Lassa fever typically occur 1-3 weeks after the patient comes into contact with the virus. These include fever, retrosternal pain, sore throat, back pain, cough, abdominal pain, vomiting, diarrhea, conjunctivitis, facial swelling, proteinuria, and mucosal bleeding. Neurological problems have also been described, including hearing loss, tremors, and encephalitis.

Bunyaviridae is a family of (−)-sense RNA viruses. As used herein, "bunyavirus" refers to members of the Bunyaviridae family and includes the genuses Orthobunyavirus, Hantavirus, Phlebovirus, and Nairovirus.

Hantavirus infection is spread from rodents (reservoir) to man by aerosolized feces, not insect vector, causing hantavirus pulmonary syndrome (HPS). Patients with HPS typically present in with a relatively short febrile prodrome lasting 3-5 days. In addition to fever and myalgias, early symptoms include headache, chills, dizziness, non-productive cough, nausea, vomiting, and other gastrointestinal symptoms. Malaise, diarrhea, and lightheadedness are reported by approximately half of all patients, with less frequent reports of arthralgias, back pain, and abdominal pain. Patients may report shortness of breath, (respiratory rate usually 26-30 times per minute). Typical findings on initial presentation include fever, tachypnea and tachycardia. The physical examination is usually otherwise normal.

In man, the Phlebovirus Rift valley fever virus produces an acute, flu-like illness and is transmitted by mosquitoes from animal reservoirs (e.g. sheep) to man. Sand fly fever is transmitted to man by Phlebotomous flies (sand-flies) and causes an acute, febrile illness characterized by fever, malaise, eye pain, and headache.

Hendra and Nipah virus in the Henipavirus genus of the subfamily Paramyxovirinae are distinguished by fatal disease in both animal and human hosts. In particular, the high mortality and person-to-person transmission associated with the most recent Nipah virus outbreak.

The papain-like cathepsin inhibitors of the invention can be combined with other therapeutic agents. The inhibitor and other therapeutic agent may be administered simultaneously or sequentially. When the other therapeutic agents are administered simultaneously they can be administered in the same or separate formulations, but are administered at the same time. The other therapeutic agents are administered sequentially with one another and with the inhibitors, when the administration of the other therapeutic agents and the inhibitors is temporally separated. The separation in time between the administration of these compounds may be a matter of minutes or it may be longer. Other therapeutic agents include but are not limited to anti-viral vaccines and anti-viral agents. In some instances the cathepsin inhibitors are administered with multiple therapeutic agents, i.e., 2, 3, 4 or even more different anti-viral agents.

An anti-viral vaccine is a formulation composed of one or more viral antigens and one or more adjuvants. The viral antigens include proteins or fragments thereof as well as whole killed virus. Adjuvants are well known to those of skill in the art.

Antiviral agents are compounds which prevent infection of cells by viruses or replication of the virus within the cell. There are many fewer antiviral drugs than antibacterial drugs because viruses are more dependent on host cell factors than bacteria. There are several stages within the process of viral infection which can be blocked or inhibited by antiviral agents. These stages include, attachment of the virus to the host cell (immunoglobulin or binding peptides), membrane penetration inhibitors, e.g. T-20, uncoating of the virus (e.g. amantadine), synthesis or translation of viral mRNA (e.g. interferon), replication of viral RNA or DNA (e.g. nucleotide analogues), maturation of new virus proteins (e.g. protease inhibitors), and budding and release of the virus.

Nucleotide analogues are synthetic compounds which are similar to nucleotides, but which have an incomplete or abnormal deoxyribose or ribose group. Once the nucleotide analogues are in the cell, they are phosphorylated, producing the triphosphate formed which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, zidovudine (azidothymidine), imiquimod, and resimiquimod.

The interferons are cytokines which are secreted by virus-infected cells as well as immune cells. The interferons function by binding to specific receptors on cells adjacent to the infected cells, causing the change in the cell which protects it from infection by the virus. α and β-interferon also induce the expression of Class I and Class II MHC molecules on the surface of infected cells, resulting in increased antigen presentation for host immune cell recognition. α and β-interferons are available as recombinant forms and have been used for the treatment of chronic hepatitis B and C infection. At the dosages which are effective for anti-viral therapy, interferons have severe side effects such as fever, malaise and weight loss.

Anti-viral agents which may be useful in combination with the inhibitors of the invention include but are not limited to immunoglobulins, amantadine, interferons, nucleotide analogues, and other protease inhibitors (other than the papain-like cysteine protease inhibitors—although combinations of papain-like cysteine protease inhibitors are also useful). Specific examples of anti-viral agents include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Immunoglobulin therapy is used for the prevention of viral infection. Immunoglobulin therapy for viral infections is different than bacterial infections, because rather than being antigen-specific, the immunoglobulin therapy functions by binding to extracellular virions and preventing them from attaching to and entering cells which are susceptible to the viral infection. The therapy is useful for the prevention of viral infection for the period of time that the antibodies are present in the host. In general there are two types of immunoglobulin therapies, normal immunoglobulin therapy and hyper-immunoglobulin therapy. Normal immune globulin therapy utilizes a antibody product which is prepared from the serum of normal blood donors and pooled. This pooled product contains low titers of antibody to a wide range of human viruses, such as hepatitis A, parvovirus, enterovirus (especially in neonates). Hyper-immune globulin therapy utilizes antibodies which are prepared from the serum of individuals who have high titers of an antibody to a particular virus. Those antibodies are then used against a specific virus. Another type of immunoglobulin therapy is active immunization. This involves the administration of antibodies or antibody fragments to viral surface proteins.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the inhibitor can be administered to a subject by any mode that delivers the inhibitor to the desired surface. Administering the pharmaceutical composition of the present invention may be accomplished by any means known to the skilled artisan. Preferred routes of administration include but are not limited to oral, intrathecal, intra-arterial, direct bronchial application, parenteral (e.g. intravenous), intramuscular, intranasal, sublingual, intratracheal, inhalation, ocular, vaginal, and rectal, e.g., using a suppository.

For oral administration, the compounds (i.e., inhibitors, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified or mixed with other components so that oral delivery of the derivative is efficacious. Generally, the chemical modification or mixture contemplated permits (a) longer half-lives; and (b) uptake into the blood stream from the stomach or intestine. Also desired is the increase in overall stability of the component or components and increase in circulation time in the body. Examples of such moieties or other compounds include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: Enzymes as Drugs, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the inhibitor (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the inhibitor (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the inhibitor or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

The invention also includes kits. The kit has a container housing a papain-like cysteine protease inhibitor and optionally additional containers with other therapeutics such as anti-viral agents or viral vaccines. The kit also includes instructions for administering the component(s) to a subject who has or is at risk of having an enveloped viral infection.

In some aspects of the invention, the kit can include a pharmaceutical preparation vial, a pharmaceutical preparation diluent vial, and inhibitor. The vial containing the diluent for the pharmaceutical preparation is optional. The diluent vial contains a diluent such as physiological saline for diluting what could be a concentrated solution or lyophilized powder of inhibitor. The instructions can include instructions for mixing a particular amount of the diluent with a particular amount of the concentrated pharmaceutical preparation, whereby a final formulation for injection or infusion is prepared. The instructions may include instructions for use in an oral formulation, inhaler, intravenous injection or any other device useful according to the invention. The instructions can include instructions for treating a patient with an effective amount of inhibitor. It also will be understood that the containers containing the preparations, whether the container is a bottle, a vial with a septum, an ampoule with a septum, an infusion bag, and the like, can contain indicia such as conventional markings which change color when the preparation has been autoclaved or otherwise sterilized.

In addition to the traditional inhibitors described above, papain-like cysteine proteases can also be inhibited by antisense and RNAi mechanisms. Thus, the invention embraces antisense oligonucleotides that selectively bind to nucleic acid molecules encoding a papain-like cysteine proteases to decrease expression and activity of this protein and subunits thereof.

As used herein, the term “antisense oligonucleotide” or “antisense” describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Antisense oligonucleotides that selectively bind to a nucleic acid molecule encoding a papain-like cysteine protease are particularly preferred. Those skilled in the art will recognize that the exact length of the antisense oligonucleotide and its degree of complementarity with its target will depend upon the specific target selected, including the sequence of the target and the particular bases which comprise that sequence.

It is preferred that the antisense oligonucleotide be constructed and arranged so as to bind selectively with the target under physiological conditions, i.e., to hybridize substantially more to the target sequence than to any other sequence in the target cell under physiological conditions. Based upon the nucleotide sequences of nucleic acid molecules encoding papain-like cysteine protease, (e.g., GenBank Accession Nos. BC010240, for Cathepsin B, or BC012612, for Cathepsin L) or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least about 10 and, more preferably, at least about 15 consecutive bases which are complementary to the target, although in certain cases modified oligonucleotides as short as 7 bases in length have been used successfully as antisense oligonucleotides. See Wagner et al., Nat. Med. 1(11): 1116-1118, 1995. Most preferably, the antisense oligonucleotides comprise a complementary sequence of 20-30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., Cell Mol. Neurobiol. 14(5):439-457, 1994) and at which proteins are not expected to bind.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acid molecules has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose.

The present invention, thus, contemplates pharmaceutical preparations containing modified antisense molecules that are complementary to and hybridizable with, under physiological conditions, nucleic acid molecules encoding a papain-like cysteine protease, together with pharmaceutically acceptable carriers. Antisense oligonucleotides may be administered as part of a pharmaceutical composition. In this latter embodiment, it may be preferable that a slow intravenous administration be used. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a subject.

The methods of the invention also encompass use of isolated short RNA that directs the sequence-specific degradation of a papain-like cysteine protease mRNA through a process known as RNA interference (RNAi). The process is known to occur in a wide variety of organisms, including embryos of mammals and other vertebrates. It has been demonstrated that dsRNA is processed to RNA segments 21-23 nucleotides (nt) in length, and furthermore, that they mediate RNA interference in the absence of longer dsRNA. Thus, these 21-23 nt fragments are sequence-specific mediators of RNA degradation and are referred to herein as siRNA or RNAi. Methods of the invention encompass the use of these fragments (or recombinantly produced or chemically synthesized oligonucleotides of the same or similar nature) to enable the targeting of papain-like cysteine protease mRNAs for degradation in mammalian cells useful in the therapeutic applications discussed herein.

The methods for design of the RNA's that mediate RNAi and the methods for transfection of the RNAs into cells and animals is well known in the art and are readily commercially available (Verma N. K. et al, J. Clin. Pharm. Ther., 28(5):395-404 (2004), Mello C. C. et al. Nature, 431(7006)338-42 (2004), Dykxhoorn D. M. et al., Nat. Rev. Mol. Cell Biol. 4(6):457-67 (2003) *Proligo* (Hamburg, Germany), *Dharmacon Research* (Lafayette, Colo., USA), Pierce Chemical (part of *Perbio Science*, Rockford, Ill., USA), *Glen Research* (Sterling, Va., USA), *ChemGenes* (Ashland, Mass., USA), and *Cruachem* (Glasgow, UK)). The RNAs are preferably chemically synthesized using appropriately protected ribonucleoside phosphoramidites and a conventional DNA/RNA synthesizer. Most conveniently, siRNAs are obtained from commercial RNA oligo synthesis suppliers listed herein. In general, RNAs are not too difficult to synthesize and are readily provided in a quality suitable for RNAi. A typical 0.2 μmol-scale RNA synthesis provides about 1 milligram of RNA, which is sufficient for 1000 transfection experiments using a 24-well tissue culture plate format.

The papain-like cysteine protease cDNA specific siRNA is designed preferably by selecting a sequence that is not within 50-100 bp of the start codon and the termination codon, avoids intron regions, avoids stretches of 4 or more bases such as AAAA, CCCC, avoids regions with GC content <30% or >60%, avoids repeats and low complex sequence, and it avoids single nucleotide polymorphism sites. The papain-like cysteine protease siRNA may be designed by a search for a 23-nt sequence motif AA(N19). If no suitable sequence is found, then a 23-nt sequence motif NA(N21) may be used with conversion of the 3' end of the sense siRNA to TT. Alternatively, the papain-like cysteine protease siRNA can be designed by a search for NAR(N17)YNN. The target sequence may have a GC content of around 50%. The siRNA targeted sequence may be further evaluated using a BLAST homology search to avoid off target effects on other genes or sequences. Negative controls are designed by scrambling targeted siRNA sequences. The control RNA preferably has the same length and nucleotide composition as the siRNA but has at least 4-5 bases mismatched to the siRNA. The RNA molecules of the present invention can comprise a 3' hydroxyl group. The RNA molecules can be single-stranded or double stranded; such molecules can be blunt ended or comprise overhanging ends (e.g., 5', 3') from about 1 to about 6 nucleotides in length (e.g., pyrimidine nucleotides, purine nucleotides). In order to further enhance the stability of the RNA of the present invention, the 3' overhangs can be stabilized against degradation. The RNA can be stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

The RNA molecules used in the methods of the present invention can be obtained using a number of techniques known to those of skill in the art. For example, the RNA can be chemically synthesized or recombinantly produced using methods known in the art. Such methods are described in U.S. Published Patent Application Nos. US2002-0086356A1 and US2003-0206884A1 that are hereby incorporated by reference in their entirety.

The methods described herein are used to identify or obtain RNA molecules that are useful as sequence-specific mediators of papain-like cysteine protease mRNA degradation and, thus, for inhibiting papain-like cysteine protease activity. Expression of papain-like cysteine proteases can be inhibited in humans in order to prevent the protein from being translated and thus contributing to the viral entry process.

The RNA molecules may also be isolated using a number of techniques known to those of skill in the art. For example, gel electrophoresis can be used to separate RNAs from the combination, gel slices comprising the RNA sequences removed and RNAs eluted from the gel slices. Alternatively, non-denaturing methods, such as non-denaturing column chromatography, can be used to isolate the RNA produced. In addition, chromatography (e.g., size exclusion chromatography), glycerol gradient centrifugation, affinity purification with antibody can be used to isolate RNAs.

Any RNA can be used in the methods of the present invention, provided that it has sufficient homology to the papain-like cysteine protease gene to mediate RNAi. The RNA for use in the present invention can correspond to the entire papain-like cysteine protease gene or a portion thereof. There is no upper limit on the length of the RNA that can be used. For example, the RNA can range from about 21 base pairs (bp) of the gene to the full length of the gene or more. In one embodiment, the RNA used in the methods of the present invention is about 1000 bp in length. In another embodiment, the RNA is about 500 bp in length. In yet another embodiment, the RNA is about 22 bp in length. In certain embodiments the preferred length of the RNA of the invention is 21 to 23 nucleotides.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Introduction

Several viruses including Ebola virus (EboV) and Nipah virus cause rapidly fatal hemorrhagic fever for which there is no prevention or treatment. The following examples show that the endosomal cysteine protease cathepsin B and/or cathepsin L is an essential host factor for EboV and Nipah infection. These studies of cathepsin B function support a model in which stepwise proteolysis of the EboV glycoprotein subunit GP1 triggers membrane fusion and cell entry. A proteolytic cascade within endosomes of target cells is a novel mechanism for triggering a viral envelope glycoprotein. Cathepsin B inhibitors dramatically reduce multiplication of infectious EboV-Zaire and therefore are useful as anti-EboV drugs. Combined use of cathepsin B and cathepsin L inhibit all known species of filoviruses. Cathepsin L inhibitors also prevent cell-cell fusion mediated by Nipah virus envelope glycoproteins F and G.

Materials and Methods

Plasmids A plasmid expressing EboV GP Zaire (Mayinga strain) was generated by subcloning the GP ORF from plasmid pCB6-GP (Geisbert, et al., *Nat. Med.* 10, S110 (2004)) (a kind gift of P. Bates, Univ. of Pennsylvania, Philadelphia, Pa.) into the pcDNA3.1-(Zeo) vector (Invitrogen, Carlsbad, Calif.). pcDNA3.1-GPΔM, which lacks residues 309-489 in GP, was engineered as described (Wool-Lewis, et al., *J. Virol.* 72, 3155 (1998)). Plasmids expressing VSV G (Takada et al., *Proc. Natl. Acad. Sci. USA* 94, 14764 (1997)), human CatL (Volchkov, *Curr. Top. Microbiol. Immunol.* 235, 35 (1999)) and human CatB (Volchkov, *Curr. Top. Microbiol. Immunol.* 235, 35 (1999)) (kindly provided by T. S. Dermody, Vanderbilt Univ., Nashville, Tenn.) have been described.

Cell Lines and Antibodies Vero and 293T cells were maintained in DMEM (Invitrogen) supplemented with 10% fetal bovine serum (Hyclone, Logan, Utah). MEFs derived from wild-type and CatB-knockout mice (kindly provided by T. S. Dermody) have been described previously (Sanchez et al., *J. Virol.* 72, 6442 (1998)). MEFs lacking both CatB and CatL were derived from $CatB^{-/-}$:$CatL^{-/-}$ double-knockout mice (U. Felbor et al., Proc Natl Acad Sci USA 99: 7883-(2002)). EboV GP was detected by immunoblotting with a GP/sGP-specific antiserum kindly provided by A. Sanchez (CDC, Atlanta, Ga.) (1:20000 dilution). Immunoblots were probed with secondary antibodies conjugated to horseradish peroxidase (1:5000 dilution) (Sigma, St Louis, Mo.), and developed using an enhanced chemiluminescence protocol (Perkin Elmer, Boston, Mass.).

Construction of VSVΔG-GFP Recombinant Virus A VSV cDNA lacking the G gene (pVSVΔG) was generated from plasmids encoding VSV recombinants MIG and GIL (Jeffers, et al., *J. Virol.* 76, 12463 (2002)). This recombinant plasmid contained a 65-nt sequence comprising the VSV gene start and end sequences flanking a stuffer sequence in place of the G gene. The green fluorescent protein (GFP) ORF was amplified from pGreen-Lantern (Invitrogen) and inserted between the leader and N genes of VSV by cloning into pVSV(+)41 (Weissenhorn, et al., *Mol Cell* 2, 605 (1998)), to generate pVSV1(+)-GFP. Plasmids pVSVΔG and pVSV1(+) GFP were used to generate pVSVΔG-GFP using standard cloning techniques. Virus was recovered, amplified, and purified as described (Ito, et al., *J. Virol.* 73, 8907 (1999)), except that a plasmid expressing VSV G was transfected into cells at each passage.

VSV Pseudotypes Viruses bearing VSV G, EboV GP, EboV GPΔM, or Marburg GP were generated essentially as described (Simmons et al., *Virology* 305, 115 (2003)). Briefly, 293T cells were transfected with a plasmid expressing an envelope glycoprotein, using Lipofectamine 2000 (Invitrogen) according to the manufacturer's instructions. After 3648 h, cells were exposed to VSVΔG-GFP virus pseudotyped with VSV G (1 iu/cell) for 1 h at 37° C. Cells were washed to remove unbound virus, and infection was allowed to proceed for 24-36 h at 37° C. Virus-containing supernatants were then harvested, concentrated by pelleting twice through a 10% sucrose cushion, resuspended in NTE buffer (10 mM Tris.Cl [pH 7.5], 135 mM NaCl, 1 mM EDTA), and frozen at −80° C. Infectivities of VSV pseudotypes were measured by counting GFP-positive cells by fluorescence microscopy or by flow cytometry (BD FACScan). Experiments reported in FIGS. 1-3 were performed with pseudotypes bearing GPΔM rather than GP because the former were ~100-fold more infectious, and provided greater sensitivity over the background level of VSV G-dependent infectivity (0.001% vs. 0.1%, respectively). Key findings were subsequently reproduced with pseudotypes bearing GP and indicate no determinative role for the variable/mucin-like domain in requirements for endosomal cysteine proteases in Vero cells, or in susceptibility to proteolytic processing in vitro (see FIG. 1 and FIGS. 5-8). Prior to infectivity measurement, pseudotypes bearing GP were incubated with a VSV G-specific neutralizing monoclonal antibody (Skehel, et al., *Annu. Rev. Biochem.* 69, 531 (2000)) (100 μg/ml) for 30 min at room temp to reduce background infection.

Protease Inhibitor Experiments Protease inhibitors E-64d, CA074, pepstatin A, aprotinin (Sigma), and FYdmk (Z-Phe-Tyr-(tBu)-diazomethylketone; Calbiochem) were dissolved in water (aprotinin) or DMSO, and dispensed into DMEM containing 1% DMSO immediately before use. Cells were preincubated with inhibitors for 3 to 4.5 h at 37° C., and then exposed to virus. For the VSV pseudotypes, infectivity was measured 16-24 h following infection, and inhibitor was present throughout.

EboV and Marburg Infections Experiments with infectious EboV-were carried out under BSL-4 containment at the United States Army Medical Institute of Infectious Diseases (Fort Detrick, Md.). Vero cells were pretreated with E-64d (300 μM) or CA074 (80 μM) in DMEM containing 1% DMSO for 4 h, and then exposed to EboV-Zaire (1995 strain) (1 pfu/cell) (Earp, et al., *Curr. Top. Microbiol. Immunol.* 285, 25 (2005)) for 1 h in the presence of inhibitor. Cultures were then washed thoroughly, and incubated with growth medium at 37° C. At the indicated times, supernatants and cells were both harvested. Infectious virus in the supernatants was titrated by plaque assay as described (Malashkevich et al., *Proc. Natl. Acad. Sci. USA* 96, 2662 (1999)). To measure levels of cell-associated viral proteins, cells were lysed with NP40 buffer (10 mM Tris.Cl [pH 7.5], 150 mM NaCl, 1% NP40), and postnuclear supernatants were subjected to SDS-PAGE and immunoblotting with EboV GP-specific antibody (see above). β-actin was used as a loading control. In a separate experiment, the effects of the CatB inhibitor CA074 (80 mM) and the CatL inhibitor FYdmk (1 mM) alone and in combination on growth of Marburg (Musoke strain) virus were tested on Vero cells. In this experiment, cells were pre-treated with inhibitors for three hours and then exposed to 1000 iu of virus. Inhibitors were maintained throughout experiment and virus growth was monitored by immunoblot of cell lysates for accumulation of Marburg GP1 as described above. β-actin was used as a loading control.

Enzyme Assays The enzymatic activities of CatB and CatL in acidified lysates of Vero cells and MEFs were assayed with fluorogenic peptide substrates Z-Arg-Arg-AMC (Calbiochem, San Diego, Calif.) and (Z-Phe-Arg) 2-R110 (Molecular Probes, Eugene, Oreg.), respectively, as described (Volchkov, *Curr. Top. Microbiol. Immunol.* 235, 35 (1999)), but with the exception that lysates were pretreated with 1 μM FYdmk or 1 μM CA074 for 20 min at room temperature prior to assaying for CatB or CatL, respectively. These assay conditions were validated for specificity using purified human CatB and CatL (Calbiochem).

In Vitro Protease Treatments Pelleted viral preparations (0.5 to 2 μg protein) were incubated with no enzyme, purified CatL or CatB in Cat buffer (100 mM sodium acetate [pH 5.5], 1 mM EDTA, 5 mM DTT) at 37° C., and reactions were terminated by removal onto ice, followed by addition of 50 μM E-64 (Sigma), and neutralization with 100 mM Hepes [pH 7.4]. Viral particles were diluted into DMEM prior to infection. Prior to analysis of EboV GP by SDS-PAGE and immunoblotting, samples were treated with protein Nglycosidase F (New England Biolabs, Beverly, Mass.) to remove N-linked oligosaccharides according to the manufacturer's instructions.

Primary Human Macrophages. Unpooled heparinized whole blood from human volunteers was procured from Research Blood Components, L.L.C. (Brighton, Mass.). Buffy coats enriched in peripheral blood mononuclear cells (PBMCs) were isolated by centrifugation of whole blood through Ficoll-Hypaque density gradients. Buffy coats were washed twice by centrifugation, and resuspended at a concentration of ~2.5 million PBMCs/ml in RPMI-1640 medium (RPMI-10; Invitrogen, Carlsbad, Calif.) supplemented to contain 10% heat-inactivated fetal bovine serum.

Cells were plated in 48-well multiwell tissue culture plates at ~$5\times10^5$ cells/well. After 2 hours at 37° C., plates were washed twice with RPMI-10 to remove non-adherent cells, and adherent monocytes were incubated in RPMI-10 supplemented to contain 100 ng/ml granulocyte/macrophage-colony stimulating factor (GM-CSF,) to induce differentiation to macrophages. The monocyte-derived macrophages were used for infection studies.

Cell-Cell Fusion Assays: 293T human embryonic kidney cells were incubated in growth medium containing increasing concentrations of cathepsin L inhibitor FYdmk for 2 h at 37° C., and then transfected with plasmids expressing Nipah virus glycoproteins F and G and the enhanced green fluorescent protein (EGFP) using Lipofectamine 2000, according to the manufacturer's instructions. Cells were maintained in growth medium containing FYdmk for 24 hours, and syncytia were visualized by epifluorescence microscopy.

Example 1

Figures 2, 2A, 2B, 2C:
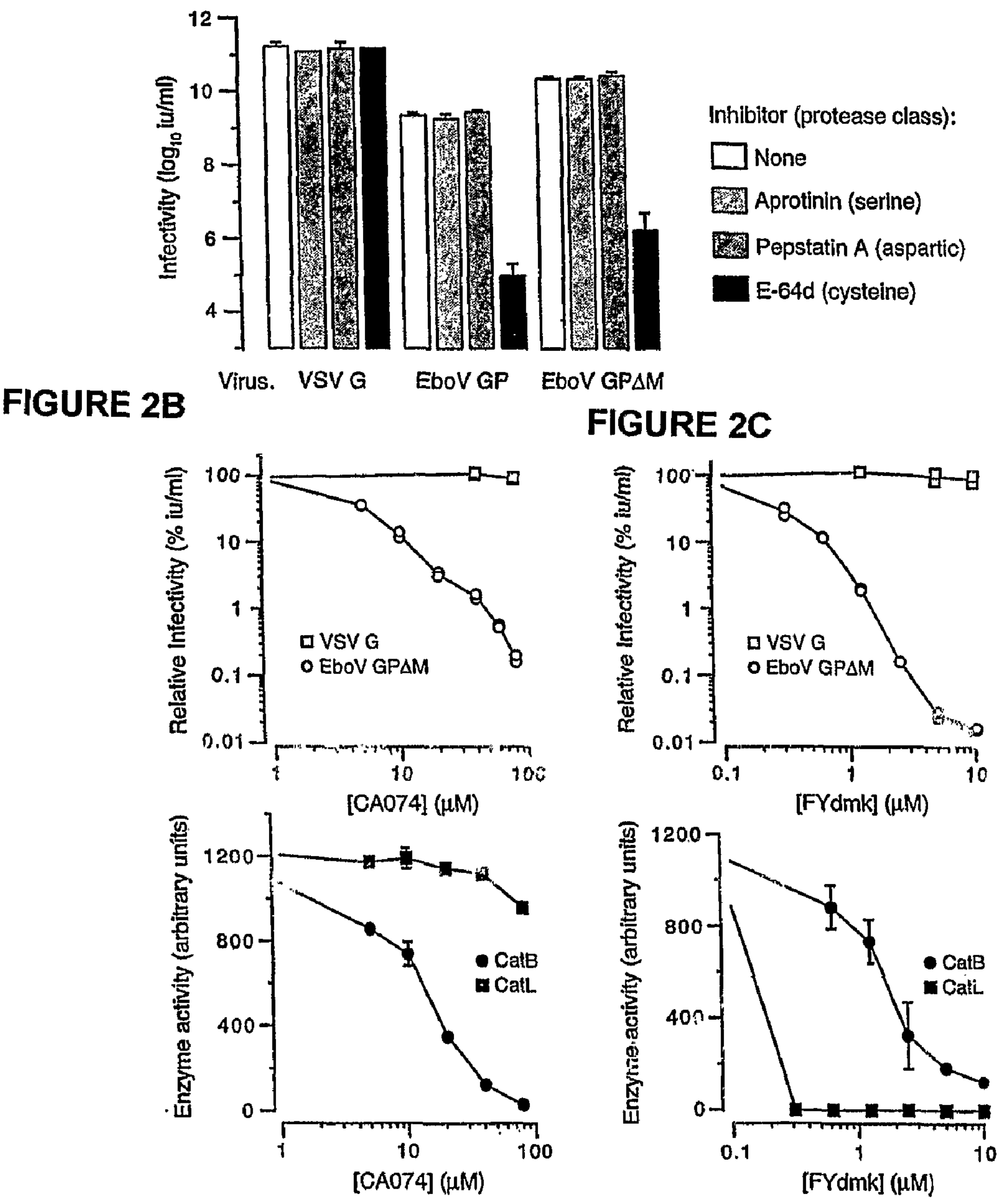
FIG. 2 is a series of graphs showing that activity of endosomal cysteine protease Cathepsin B (CatB) is involved in EboV Zaire GP dependent infection in Vero cells.
FIG. 2A shows effects of class-specific protease inhibitors on infectivities of viruses containing VSV G, EboV Zaire GP, or EboV Zaire GPΔM (ΔM and ΔMuc are used herein interchangeably). DMSO vehicle (1%) (none), aprotinin (500 μg/ml), pepstatin A (200 μM), E-64d (300 μM). The y-axis is infectivity in log 10 iu/ml.
FIG. 2B (top panel) is a graph showing the effect of CatB-selective inhibitor CA074 on infectivities of viruses containing VSV G or EboV Zaire GPΔM.
FIG. 2C is a graph showing the effects of CatL/CatB inhibitor FYdmk on infectivities (top panel) and enzyme activities (bottom panel). The y-axes, top panels, of FIGS. 2B and 2C are relative infectivity (% iu/ml) and y-axes, bottom panels, are enzyme activities in arbitrary units. The x-axes are inhibitor concentrations given in μM. Error bars, s.d. (n=3).

To test the possibility that acid-dependent endosomal proteases are host factors for EboV GP-dependent cell entry, the capacity of broad-spectrum protease inhibitors to block infection by vesicular stomatitis virus (VSV) particles pseudotyped with EboV Zaire GP-was assessed (FIG. 2A). The cysteine protease inhibitor E-64d reduced GP-dependent infection in Vero cells by ~99.99% (FIG. 2A). In contrast, serine or aspartic protease inhibitors had no detectable effect on viral infectivity. A similar profile of inhibition was observed with more highly infectious viral particles containing a form of EboV Zaire GP that lacks the mucin-like/variable domain in GP1 (GPΔM) (Jeffers, et al., *J. Virol.* 76, 12463 (2002)). The effect of E-64d was specific to the EboV Zaire glycoproteins: VSV particles containing acid-dependent glycoproteins VSV G (FIG. 2A) or ALV retrovirus Env were not significantly inhibited. Furthermore, treatment of viral particles with E-64d did not reduce their infectivity in untreated cells. These findings indicated that a cysteine protease expressed within target Vero cells is required for EboV GP-dependent cell entry.

Figures 6, 6A, 6B:
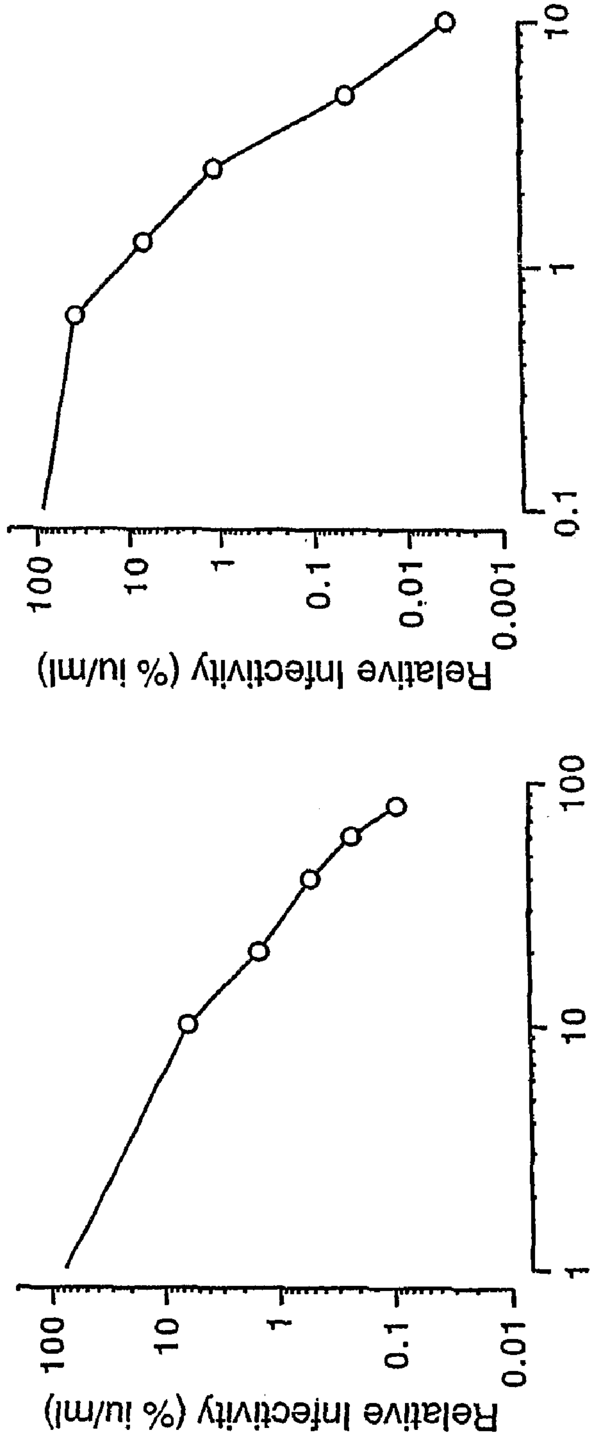
FIG. 6 is two graphs showing the activity of endosomal cysteine protease CatB is involved in EboV GP-dependent infection in Vero cells.
FIG. 6A shows the effect of CatB-selective inhibitor CA074 on infectivity of virus containing EboV Zaire GP.
FIG. 6B shows the effect of CatL/CatB inhibitor FYdmk on infectivity. Averages of duplicate trials are shown. The y-axes are relative infectivity in % iu/ml, and the x-axis are concentrations of inhibitor in μM.

Cathepsin B (CatB) and cathepsin L (CatL) are E-64d-sensitive enzymes that are present in endosomes and lysosomes and active at acidic pH in the broad range of mammalian cells susceptible to EboV Zaire infection (Wool-Lewis, et al., *J. Virol.* 72, 3155 (1998); Turk, et al., *Biol. Chem.* 378, 141 (1997); and Otto, et al., *Chem. Rev.* 97, 133 (1997)). To examine the roles of these enzymes, we studied the effect of a selective CatB inhibitor [CA074 (Murata et al., *FEBS Lett.* 280, 307 (1991))] and a CatL/CatB inhibitor [FYdmk (Shaw, *Methods Enzymol.* 244, 649 (1994))] on EboV GP-dependent infection of Vero cells. Both compounds inhibited infection in a manner that correlated closely with inactivation of CatB but not CatL (FIGS. 2B, C and FIG. 6). In the absence of detectable CatB activity, infection was reduced by ~99.9% (FIG. 2B). Neither compound inhibited VSV G-dependent infection (FIGS. 2B and 2C). These data suggested that CatB is required for EboV Zaire GP-dependent cell entry.

Figure 3:
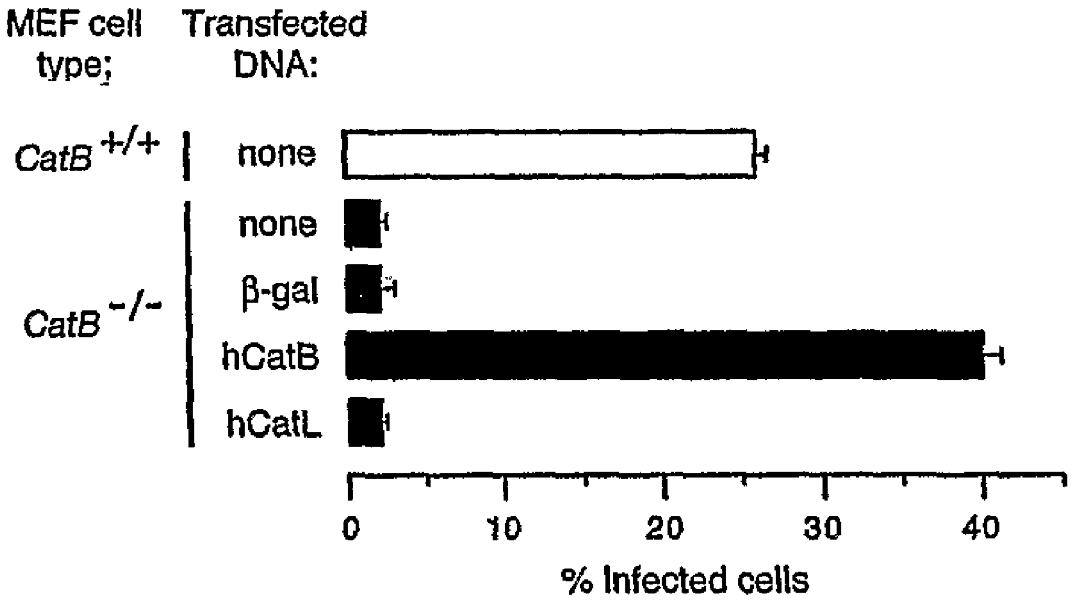
FIG. 3 is a graph showing genetic evidence that CatB is necessary for EboV Zaire GPΔM dependent infection. Wild type ($CatB^{+/+}$) and CatB-deficient ($CatB^{-/-}$) mouse embryo fibroblasts (MEFs) were left untransfected (untran), or cotransfected with plasmid DNA encoding β-galactosidase (β-gal), human CatB (hCatB), or human CatL (hCatL) and monomeric red fluorescent protein (RFP). After 24 h, cells were exposed to virus (~1 iu/cell), and the percentage of infected (GFP-positive) cells was determined 24 h later by flow cytometry. For transfected cells, the percentage of infected cells in the transfected cell population was determined ([GFP-positive and RFP-positive/RFP-positive]×100). The y-axis is % infected cells. Error bars, s.d. (n=3).

To test genetically the requirement for CatB, viral infectivity in murine embryo fibroblasts (MEFs) derived from wild-type ($CatB^{+/+}$) and CatB-knockout ($CatB^{-/-}$) mice was measured (Deussing et al., *Proc. Natl. Acad. Sci. USA* 95, 4516 (1998)). The lack of CatB activity in $CatB^{-/-}$ MEFs, and the presence of equivalent levels of CatL activity in $CatB^{+/+}$ and $CatB^{-/-}$ MEFs was confirmed by enzyme assay. A >90% reduction in EboV Zaire GP-dependent infection of $CatB^{-/-}$ MEFs was observed (FIG. 3), but no reduction was observed in VSV G-dependent infection of these cells. GP dependent infection of $CatB^{-/-}$ MEFs was completely restored by expression of human CatB (FIG. 3). Therefore, the endosomal cysteine protease CatB is an essential host factor for EboV Zaire GP-dependent cell entry.

Figure 4:
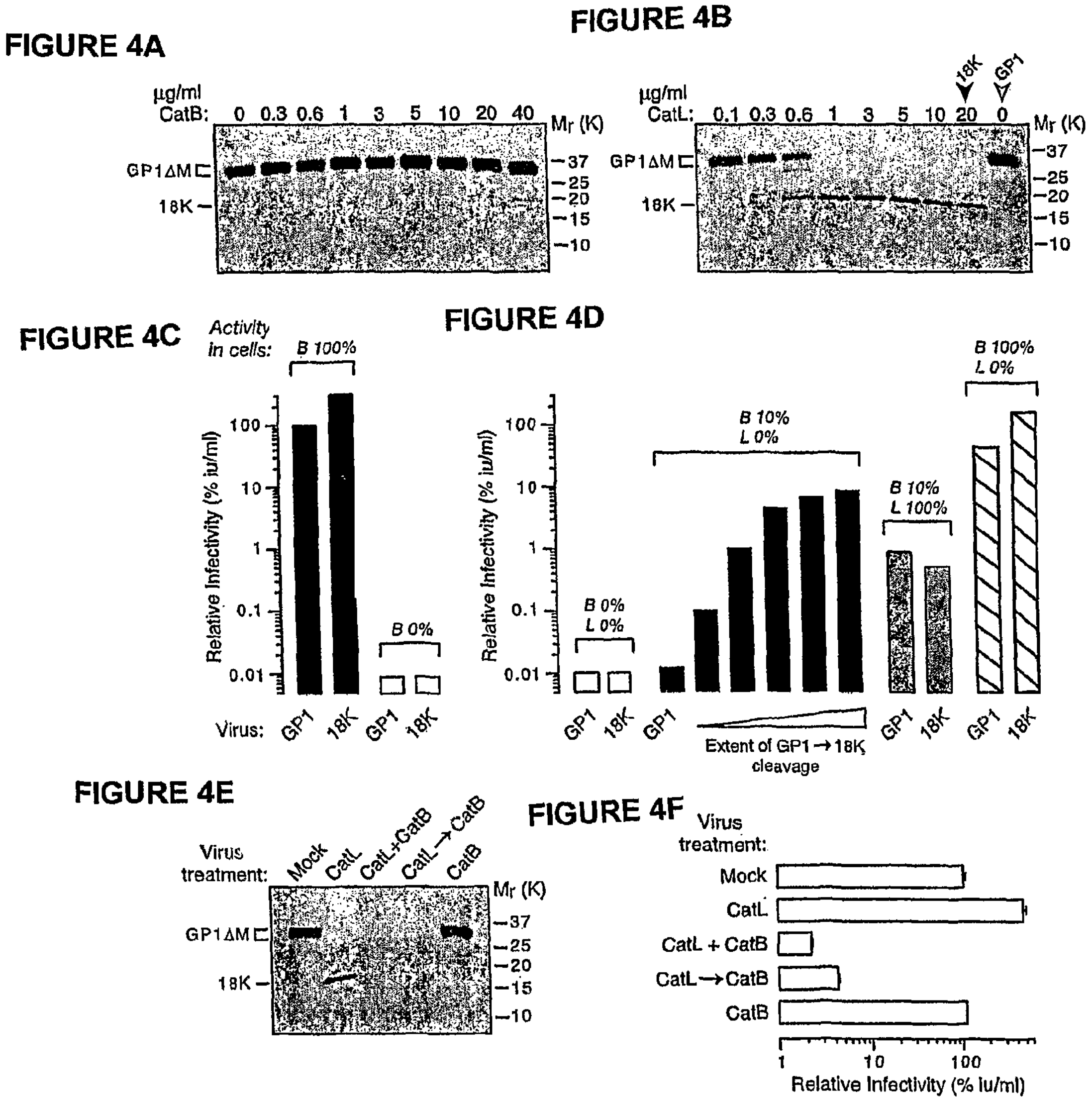
FIG. 4 is a series of graphs demonstrating that endosomal cysteine proteases act directly on EboV Zaire GPΔM to mediate infection.
Figure 7:
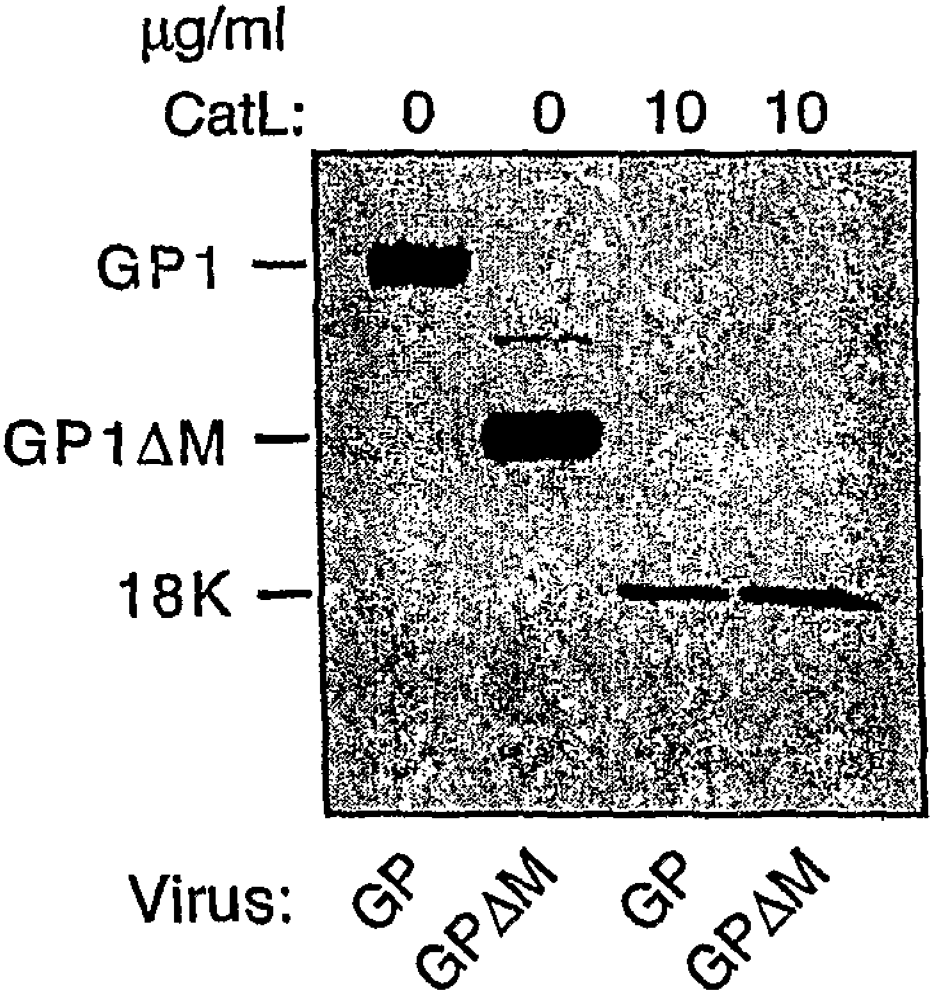
FIG. 7 is an image of a protein gel showing that purified CatL cleaves both EboV Zaire GP and GP Zaire ΔM to generate $GP1_{18K}$. Viruses containing EboV Zaire GP or GPΔM were incubated with the indicated concentration of CatL for 1 h at pH 5.5 and 37° C. The y-axis represents relative molecular weight.
Figures 8, 8A, 8B:
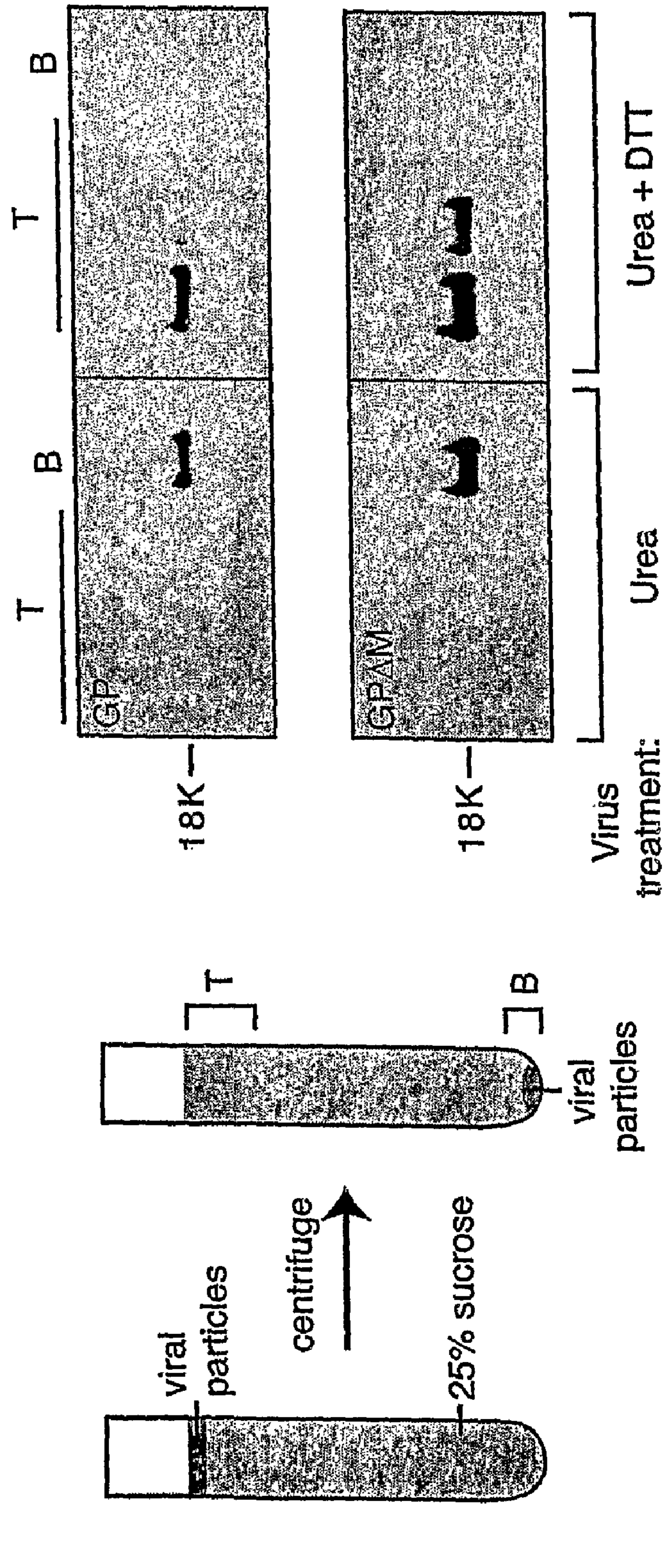
FIG. 8 is a schematic diagram and an image of protein gels showing that EboV Zaire $GP1_{18K}$ is an N-terminal fragment of GP1 that remains covalently associated to GP2 via the GP1(Cys 53)-GP2(Cys 609) disulfide bond.
FIG. 8A is a schematic diagram of experimental approach to separate viral particle-associated and released proteins.
FIG. 8B is an image of immunoblots of two SDS-PAGE of proteins. Virus containing $GP1_{18K}$ derived from GP (top panel) or GPΔM (bottom panel) (2 μg) were incubated with urea (6M) or urea and DTT (100 mM) for 30 min at 37° C. Samples were then overlaid onto a 25% sucrose cushion (0.5 ml). Viral particles were pelleted in a TLA100 rotor (Beckman) at 75000 rpm and 4° C. for 1 h. The cushion was fractionated, and three fractions from the top (T) and one fraction from the bottom (B) were subjected to SDS-PAGE and immunoblotting with anti-GP antibodies. Samples were not treated with protein N-glycosidase F prior to SDS-PAGE. The y-axis is relative molecular weight.

To investigate the role of CatB in EboV Zaire GP-dependent cell entry, the effect of purified CatB on viral particles at pH 5.5 and 37° C. was examined. CatB cleaved the GP1 subunit to yield small amounts of an ~18K N-terminal fragment ($GP1_{18K}$) (FIGS. 4A and 7-8). Although cellular CatL is dispensable for infection (FIG. 2C), purified CatL efficiently mediated GP1→$GP1_{18K}$ cleavage under these selected conditions (FIG. 4B and FIG. 7). After complete GP1→$GP1_{18K}$ cleavage, viral particles remained fully infectious and dependent upon cellular CatB activity in Vero cells (FIG. 4C) and MEFs, indicating that GP1→$GP1_{18K}$ cleavage is not the critical CatB-dependent step in cell entry.

Figure 9:
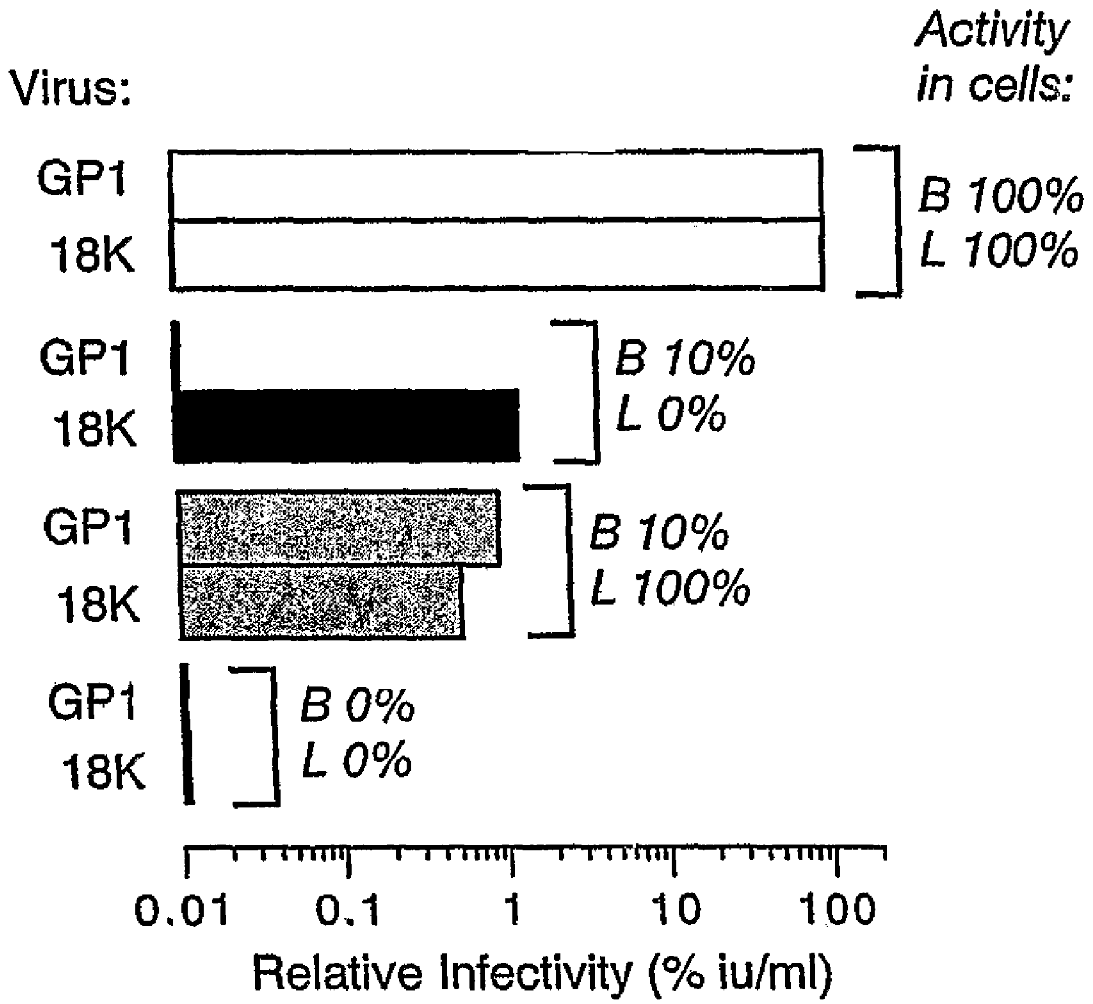
FIG. 9 is a graph demonstrating that virus containing $GP1_{18K}$ derived from EboV Zaire GP1 dramatically bypasses a block to GP1 cleavage in cells. Vero cells were treated with inhibitors to obtain the approximate levels of cellular CatB (B %) and CatL (L %) activities shown to the right of the bars. (B 100% L 100%), no drug. (B 10% L 0%), 10 μM FYdmk. (B 10% L 100%), 40 μM CA074. (B 0% L 0%), 10 μM FYdmk+40 μM CA074. Cells were then infected with virus containing GP1 (GP1) or $GP1_{18K}$ (18K) (generated by 20 μg/ml CatL treatment for 1 h at pH 5.5 and 37° C.). Averages from two trials are shown. The x-axis is relative infectivity in % iu/ml.

Based on these findings, the hypothesis that virus containing $GP1_{18K}$ is an intermediate in the CatB-dependent entry pathway was investigated. This hypothesis predicts that viral particles containing $GP1_{18K}$ should overcome a block to infection of cells in which presumptive GP1 cleavage by cellular CatB and/or CatL is inhibited. To test this prediction, cells were treated with inhibitor to reduce CatB activity to 10% and to completely inactivate CatL, and then challenged with viral particles containing increasing amounts of $GP1_{18K}$ (FIG. 4D and FIG. 9). Residual (~10%) CatB activity was necessary to carry out this experiment because virus containing $GP1_{18K}$ cannot bypass the complete loss of CatB activity (FIG. 4C). Infection of these cells was dramatically enhanced in a GP $1_{18K}$-dependent manner (by ~1000-fold) (FIG. 4D), indicating that cleavage of GP1 is an essential step in infection. In contrast, little or no $GP1_{18K}$-dependent enhancement of infection was observed in cells with fully active CatB or CatL (by <5-fold) (FIG. 4D), which strongly suggested that the cleavage of GP1 in cells that is mimicked by in vitro GP1→$GP1_{18K}$ cleavage can be mediated by either CatB or CatL. Based on these results, cleavage of GP1 by CatB and/or CatL, possibly to generate GP $1_{18K}$-like intermediate species, is necessary for EboV Zaire GP-dependent cell entry. Cellular CatB activity is required for infection by viral particles containing $GP1_{18K}$ (FIGS. 4C and 4D), indicating the existence of at least one downstream CatB-dependent event in the cell entry pathway.

To test whether further cleavage of GP1 is this event, the effect of purified CatB on viral particles containing $GP1_{18K}$ was examined. CatB, but not CatL, efficiently cleaved $GP1_{18K}$ to undetectable fragments (FIG. 4E) and reduced infectivity by >90% (FIG. 4F), suggesting that CatB cleavage of $GP1_{18K}$ prematurely released the clamp and deployed the GP2 membrane fusion machinery.

Cleavage of EboV Zaire GPΔM (FIGS. 4 and 7) and GP (FIG. 7) within VSV particles by purified CatL resulted in an ~18K GP1 fragment ($GP1_{18K}$) that remained associated with viral particles (FIG. 8). No smaller fragments were detected with the polyclonal anti-GP antiserum. These findings strongly suggest that C-terminal sequences of GP1, including GP1 residues 309-489 comprising the variable/mucin-like domain (M), are extensively cleaved during the GP1→$GP1_{18K}$ step. They suggest also that $GP1_{18K}$ is an N-terminal fragment.

In mature GP1-GP2 trimers, GP1 is disulfide-bonded to GP2 via residues Cys 53 (GP1) and Cys 609 (GP2) (Jeffers, et al., *J. Virol.* 76, 12463 (2002)). As a consequence, dissociation of GP1 from viral particles requires reduction (Wool-Lewis, et al., *J. Virol.* 73, 1419 (1999)). $GP1_{18K}$ retains this property (FIG. 8), indicating that it remains disulfide-bonded to GP2, and confirming that $GP1_{18K}$ is an N-terminal fragment of GP1 that contains Cys 53. The properties of $GP1_{18K}$ are consistent with its role as the GP1 clamp: it contains the most highly conserved GP1 amino acid sequences and structural features, including the intrasubunit and intersubunit disulfide bonds (two and one, respectively) (Jeffers, *J. Virol.* 76, 12463 (2002)).

Example 2

Figure 10:
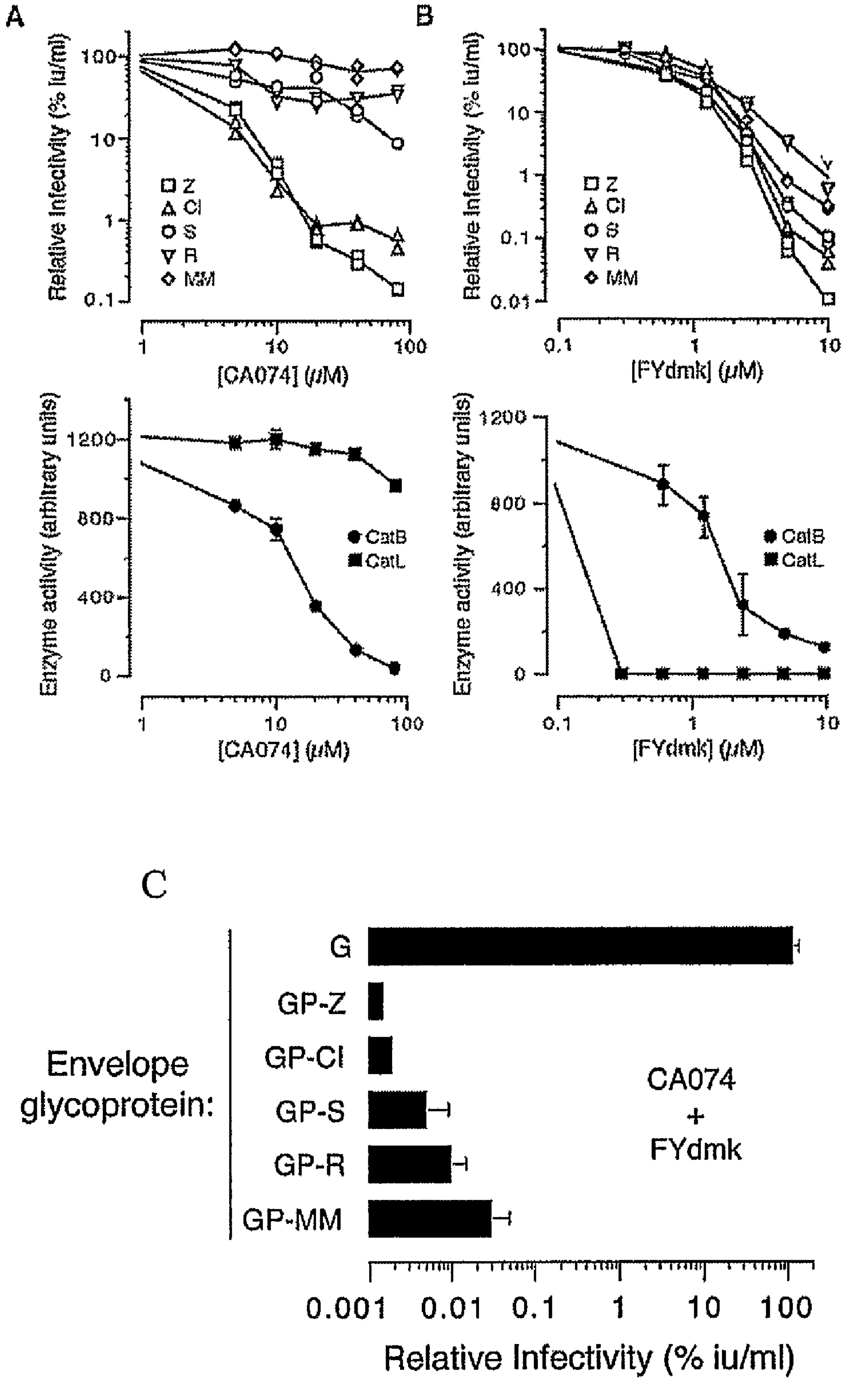
FIG. 10A is a graph showing the effect of a CatB inhibitor CA074 on the infectivity of VSV pseudotypes bearing GPs from five related species of Zaire (Z), Cote d'Ivoire (CI), Sudan (S), Reston (R) and Marburg (M) viruses (top panel) and on the corresponding CatB and CatL activities (bottom panel).
FIG. 10B is a graph showing the effect of the CatL/B inhibitor FYdmk on the infectivity of these five viruses (top panel) and on the corresponding CatB and CatL activities (bottom panel). These studies indicate that infection by GPs from Zaire and Cote d'Ivoire viruses are dependent on CatB and Sudan, Reston and Marburg viruses are dependent on either CatL or CatB. To confirm this finding, an additional experiment was performed using highly enzyme-specific concentrations of CA074 (80 μM) and FYdmk (1 μM) to inhibit CatB and CatL, respectively (FIG. 10C). It shows that these agents reduce infection by VSV (GFP) bearing Zaire, Cote d'Ivoire, Sudan, Reston and Marburg GPs ΔMs to less than 0.1% of infection of untreated Vero cells.
Figure 11:
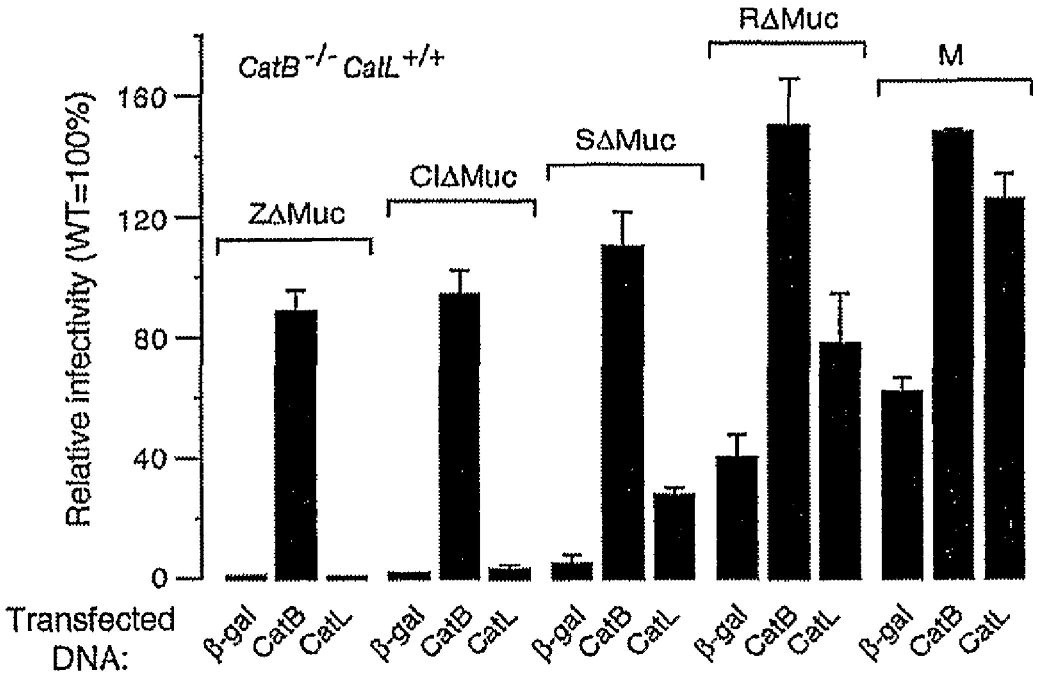
FIG. 11 provides a graph showing viral infectivities in mouse fibroblast cells lacking CatB expression ($CatB^{-/-}$) transfected with constructs encoding control (β-galactosidase), CatB or CatL enzymes. It shows that CatB expression is necessary for Zaire and Cote d'Ivoire GP infection. It also shows that CatB expression enhances infection by GPs from all five species and CatL overexpression also enhances infection by GPs from Sudan, Reston and Marburg species.

To test whether a similar mechanism of cell entry is utilized by other filovirus species, the cysteine protease inhibitors, CA074 and FYdmk were used to block host CatB and CatL activities, and infectivities of VSV particles bearing the glycoprotein from five filovirus species, Zaire (Z), Cote d'Ivoire (CI), Sudan (S), Reston (R) and Marburg (M) were examined. The Ebola GPs lacked the mucin rich domain. Relative infectivities of these species in the presence of CA074 or FYdmk at varying concentrations are shown in FIGS. 10A and 10B, respectively (top panel). The data show that the CatB-selective inhibitor, CA074 can block infection of Ebola Zaire and Cote d'Ivoire by ~99% at effective concentrations, while the infectivities of Reston and Marburg, are unaffected at the same concentrations of the inhibitor (FIG. 10A). Sudan was inhibited by 90%. In contrast, all filoviruses tested are blocked by 10 μM FYdmk, which at this concentration can inhibit both CatB and CatL activities (FIG. 10B), suggesting a role for host CatL activity for infection. This observation was confirmed using the two inhibitors as shown in FIG. 11. These results indicate that like Ebola Zaire, Cote d'Ivoire requires CatB cysteine protease for host cell entry, while Sudan, Reston and Marburg require CatL or CatB for host cell entry.

To confirm differential requirement of cellular cysteine proteases observed above, infectivities of the five filovirus species were further examined using mouse embryonic fibroblast cells genetically lacking endogenous CatB expression (FIG. 11). CatB-deficient cells were transfected with plasmid DNAs encoding β-galactosidase (β-gal), CatB or CatL and were subjected to infection with VSV particles bearing Zaire GPΔMuc, Cote d'Ivoire GPΔMuc, Sudan GPΔMuc, Reston, GPΔMuc, or Marburg-GP. Relative infectivities were measured as described previously. As shown in FIG. 11, results indicate that expression of CatB enhances infection mediated by all filoviruses GPs on CatB-deficient cells. Expression of CatL, however, only enhances infection of Ebola Sudan, Ebola Reston, and Marburg GP pseudotypes. Thus, Sudan, Reston, and Marburg GPs can use cellular CatL or CatB for host cell entry.

In support of the model that all species of filoviruses require CatB and or CatL cysteine protease activity for infection, further experiments showed that combination of CA074 and FYdmk at a concentration that specifically inhibits CatB and CatL, respectively, effectively blocked infection by GP-Zaire, GP-Cote d'Ivorie, GP-Sudan, GP-Reston or GP-Marburg, as compared to control (FIG. 10C). Together, these results indicate that CatB is necessary for Zaire and Cote d'Ivoire and either CatB or CatL is necessary for Sudan, Reston or Marburg filovirus envelope glycoprotein-mediated infection.

Example 3

The experimental results provided herein further demonstrate the essential role of cellular cysteine proteases in mediating Marburg infection. From the perspective of viral phylogeny, this is particularly insightful because as mentioned earlier Marburg virus represents one of the two branches of filovirus genuses identified thus far (along with Ebola).

Figure 12:
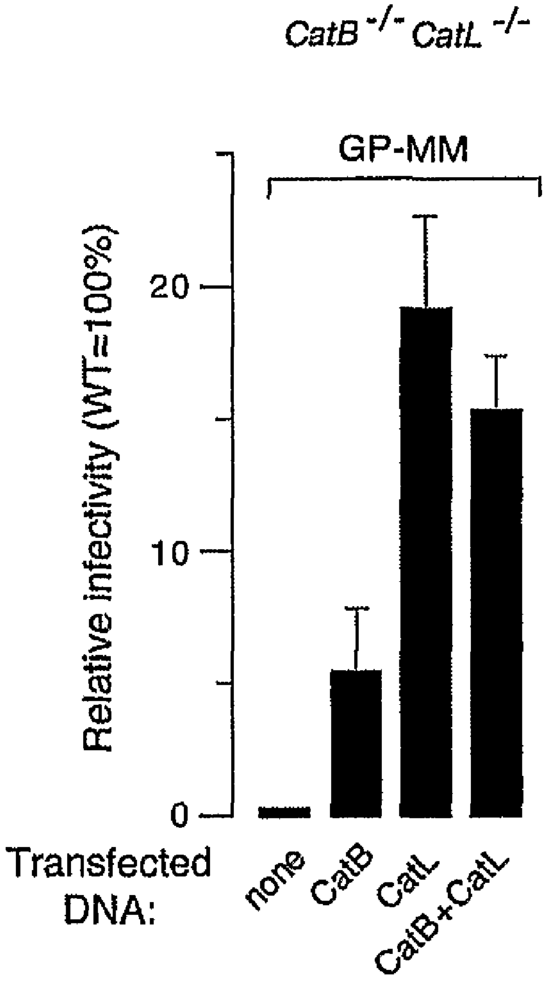
FIG. 12 is a graph showing CatB- and/or CatL-dependent VSV-GFP infection of ($CatL^{-/-}$, $CatB^{-/-}$) mouse fibroblasts mediated by Marburg virus GP. It shows that either CatL or CatB is necessary for infection of these cells.

Marburg infectivity was measured in embryonic mouse fibroblast cells lacking both CatB and CatL ($CatB^{-/-}CatL^{-/-}$), where expression of CatB, CatL or both was reconstituted back to the cells by transfection to examine the effect of the protease on infectivity by the virus. As shown in FIG. 12, expression of either CatB or CatL or both proteases is sufficient to confer Marburg virus GP-dependent infection on mouse fibroblasts deficient in both CatB and CatL genes.

Vero cells were used to further investigate the effects of inhibiting cysteine protease activities on Marburg virus infection. Marburg virus growth, as measured by accumulation of Marburg glycoprotein in protein immunoblot, is markedly reduced 66 hours after infection in Vero cells treated with CA074 (80 μM) to block cellular CatB and with FYdmk (1 μM) to block CatL (FIG. 13). This is not due to alterations in cell viability, as data show that expression of β-actin as control is not affected by inhibitor treatment (FIG. 13, right panel). Thus, inhibition of cellular CatB and CatL blocks Marburg infection of Vero cells.

Example 4

Figure 14:
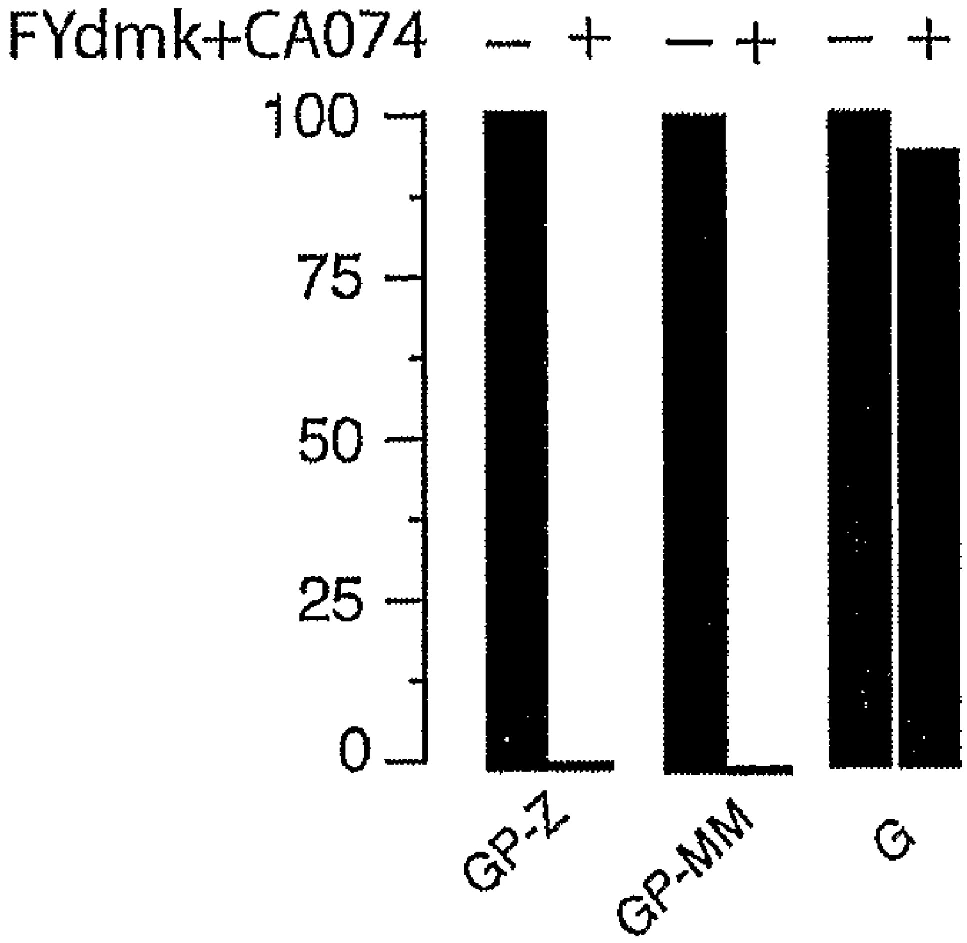
FIG. 14 is a graph showing effects of blocking CatL (FYdmk 1 μM) and CatB (CA074 80 μM) on infection of primary human macrophages by VSV particles bearing the glycoprotein of Ebola Zaire (GP-Z), Marburg (GP-MM), or its own (G). The experiment was performed because macrophages and related cells are the principal site of filovirus replication in vivo.

Primary human macrophages were used in this example to examine the effect of inhibiting cellular CatB and CatL on infection by both Ebola Zaire GP and Marburg GP-dependent infection. Human macrophages were obtained from human donors and were pretreated with both CA074 and FYdmk at concentrations of 80 and 1; subsequently cells were subjected to infection by VSV particles bearing glycoproteins of Ebola Zaire (GP-Z), glycoprotein of Marburg (GP-MM) or control (G). Data show that inhibition of CatL and CatB reduced infection (>99.9%) of primary human macrophages by GP-Z and GP-MM, but not by VSV-G (FIG. 14), again demonstrating the essential role for cellular CatB and CatL in mediating human macrophage infection by both genuses of the filovirus family.

Example 5

Figure 15:
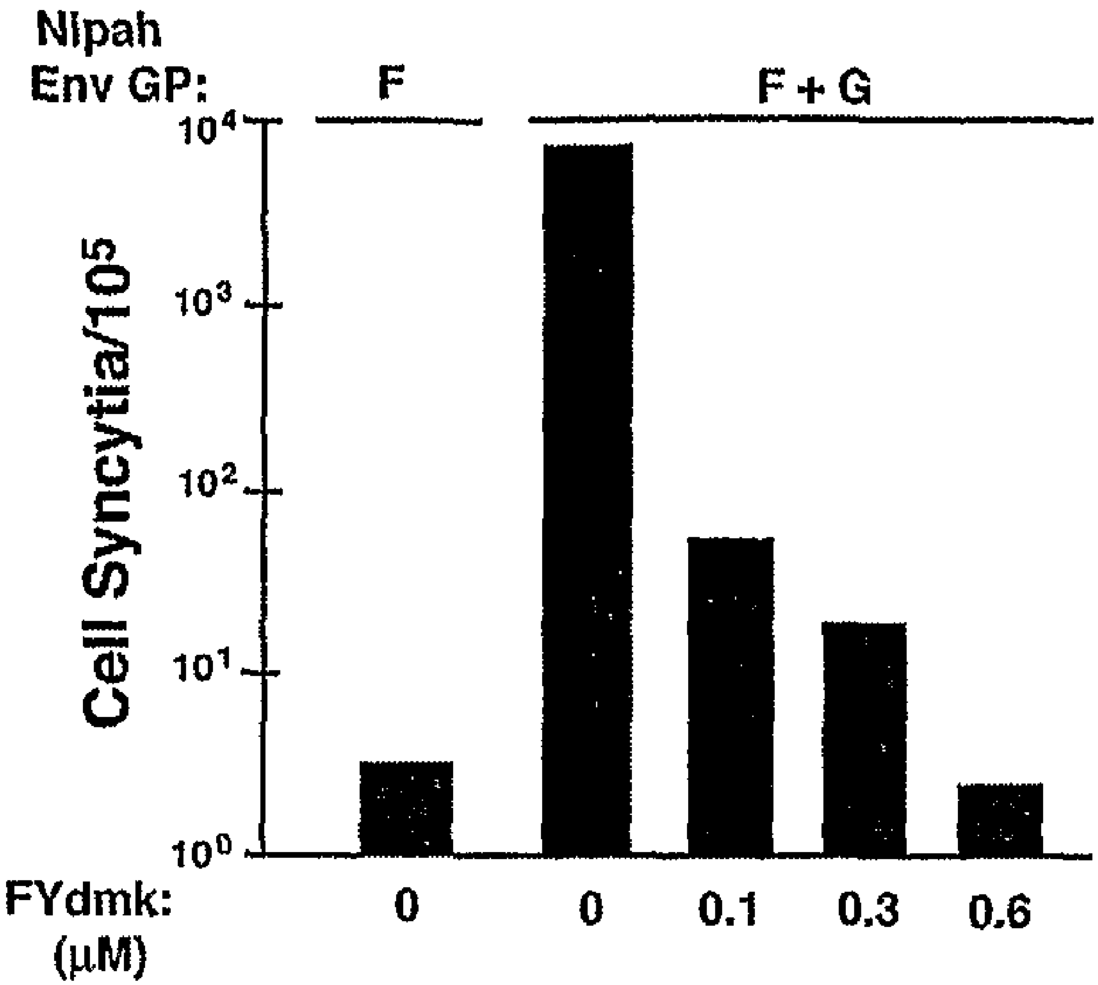
FIG. 15 is a graph demonstrating that cathepsin L inhibitor FYdmk inhibits cell-cell fusion mediated by Nipah virus H/F glycoproteins. This indicates that CatL inhibitors prevent the function of the Nipah F/G-dependent entry machinery. Nipah virus is a highly pathogenic paramyxovirus. Expression of the Nipah virus envelope glycoproteins, H and F, induces fusion to the cell membrane of adjacent contacting cells, analogous to the fusion of the Nipah virus bearing H/F during infection.

293T cells were used in this example to examine the effect of inhibiting cellular CatL on cell-cell fusion by H/F glycoproteins of Nipah virus. Cells were pretreated with 0.1 μM, 0.3 μM, or 0.6 μM FYdmk. Controls received no FYdmk. Subsequently cells were transfected with plasmids encoding Nipah virus glycoproteins F alone or F and G (GP-F or F+G). F alone served as a negative control, resulting in no fused cells. The findings (shown in FIG. 15) demonstrate that inhibition of CatL by FYdmk dramatically reduces cell-cell fusion by GP-F+GP-G, demonstrating the essential role for cellular CatL in mediating human 293T cell fusion by Nipah H/F glycoproteins, analogous to the function of these virus glycoproteins in mediating Nipah virus infection.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A method for inhibiting infection by an enveloped virus in a subject, comprising:

administering to a subject in need thereof a cathepsin inhibitor in an effective amount for inhibiting viral entry wherein the enveloped virus is a filovirus and wherein the cathepsin inhibitor is selected from the group consisting of cathepsin-B inhibitor and cathepsin- L inhibitor, wherein the cathepsin inhibitor is not a lysosomotropic agent.

2. A method for inhibiting infection by an enveloped virus in a subject, comprising administering to a subject in need thereof a cathepsin inhibitor in an effective amount for inhibiting viral entry wherein the enveloped virus is a filovirus and wherein the cathepsin inhibitor is one or more cathepsin-B or cathepsin-L inhibitors selected from a group consisting of epoxysuccinyl peptide derivatives selected from the group consisting of E-64, E-64a, E-64b, E-64c, E-64d, CA-074, CA-074 Me, CA-030, and CA-028, peptidyl aldehyde derivatives selected from the group consisting of leupeptin, antipain, chymostatin, Ac-LVK-CHO, Z-Phe-Tyr-CHO, Z-Phe-Tyr (OtBu)-COCHO.$H_2O$, 1-Naphthalenesulfonyl-Ile-Trp-CHO, and Z-Phe-Leu-COCHO.H2O, peptidyl semicarbazone, peptidyl methylketone, peptidyl trifluoromethylketone derivatives selected from the group consisting of Biotin-Phe-Ala-fluoromethyl ketone, Z-Leu-Leu-Leu-fluoromethyl ketone minimum, Z-Phe-Phe-fluoromethyl ketone, N-Methoxysuccinyl-Phe-HOMO-Phe-fluoromethyl ketone, Z-Leu-Leu-Tyr-fluoromethyl ketone, Leupeptin trifluoroacetate, and ketone, bis(acylamino)ketone [1,3-Bis(CBZ-Leu-NH)-2-propanone, peptidyl diazomethanes, Z-Phe-Ala-CHN2, Z-Phe-Thr(OBz1)-CHN2, Z-Phe-Tyr (O-t-But)-CHN2, Z-Leu-Leu-Tyr-CHN2, peptidyl acyloxymethyl ketones, peptidyl methylsulfonium salts, peptidyl vinyl sulfones, peptidyl nitriles, 2-nitrobenzoic acid, azapeptides, azobenzenes, O-acylhydroxamates, Cystatins A, B, C, stefins, kininogens, Procathepsin B Fragment 26-50, and Procathepsin B Fragment 36-50.

3. The method of claim 1, wherein the filovirus is an Ebola virus.

4. The method of claim 1, wherein the filovirus is a Marburg virus.

5. The method of claim 1, wherein the cathepsin inhibitor is administered orally.

6. The method of claim 1, wherein the cathepsin inhibitor is administered intravenously.

7. The method of claim 1, wherein multiple doses of the cathepsin inhibitor are administered.

8. The method of claim 1, wherein the cathepsin inhibitor is administered every 12 hours.

9. The method of claim 1, wherein the cathepsin inhibitor is administered in combination with another protease inhibitor.

10. The method of claim 1, wherein the subject is a human.

11. The method of claim 1, wherein the subject is a non-human animal.

12. The method of claim 1, wherein the cathepsin inhibitor is one or more selected from a group consisting of E-64, E-64d, CA-074, CA-074 Me, and leupeptin.

* * * * *